(12) United States Patent
Kwon

(10) Patent No.: US 8,460,529 B2
(45) Date of Patent: Jun. 11, 2013

(54) DEGRADABLE POLYACRYLAMIDE GEL

(75) Inventor: Young Jik Kwon, Irvine, CA (US)

(73) Assignee: Case Western Reserve University, Cleveland, OH (US)

( * ) Notice: Subject to any disclaimer, the term of this patent is extended or adjusted under 35 U.S.C. 154(b) by 113 days.

(21) Appl. No.: 12/942,636

(22) Filed: Nov. 9, 2010

(65) Prior Publication Data

US 2011/0104661 A1 May 5, 2011

Related U.S. Application Data

(63) Continuation-in-part of application No. 12/051,680, filed on Mar. 19, 2008.

(60) Provisional application No. 61/259,417, filed on Nov. 9, 2009.

(51) Int. Cl.
*B01D 57/02* (2006.01)
*G01N 27/447* (2006.01)

(52) U.S. Cl.
USPC .......................................... 204/469; 204/456

(58) Field of Classification Search
USPC .............................. 204/456–470; 435/173.9
See application file for complete search history.

(56) References Cited

U.S. PATENT DOCUMENTS
5,225,062 A * 7/1993 Yoshioka et al. ............. 204/469

OTHER PUBLICATIONS

Kwon, Y. J., et al. "Direct Antigen Presentation Using Polymeric Microparticulate Carriers Degradable at Lysosomal pH for Controlled Immune Responses", Molecular Pharmaceutics, vol. 2, No. 1, Feb. 2005, p. 83-91.*

* cited by examiner

*Primary Examiner* — J. Christopher Ball
(74) *Attorney, Agent, or Firm* — Tarolli, Sundheim, Covell & Tumminno LLP

(57) ABSTRACT

A degradable polyacrylamide gel for analyzing or separating at least one macromolecule in a sample using electrophoresis includes a polyacrylamide cross-linked with at least one degradable cross-linker having a ketal or acetal group with the formula (I), wherein $R_1$ and $R_2$ are the same or different and are hydrogen, an alkyl, or a substituted alkyl.

7 Claims, 18 Drawing Sheets

Figs. 13A-C

DEGRADABLE POLYACRYLAMIDE GEL

RELATED APPLICATION

This application claims priority from U.S. Provisional Application No. 61/259,417, filed Nov. 9, 2009, and is a continuation-in-part of Ser. No. 12/051,680, filed Mar. 19, 2008, the subject matter, which is incorporated herein by reference.

TECHNICAL FIELD

The application generally relates to gel electrophoresis, and more particularly to a degradable polyacrylamide gel for separating or analyzing at least one macromolecule in a sample.

BACKGROUND

Biomacromolecules including polysaccharides, proteins, and nucleic acids are not only building blocks of life but also key mediators of a variety of biological processes. Among them, nucleic acids are templates (e.g., chromosomal DNA) for other biomacromolecules as well as genetic regulators (e.g., microRNA and small interfering RNA (siRNA)) of molecular events. Therefore, it is essential to understand the dynamic roles of nucleic acids in normal and abnormal (diseased) biological processes, starting from separating and isolating a number of nucleic acids from biological samples. Gel electrophoresis offers simultaneous separation of many nucleic acids with high resolution. Usually agarose gels are used to electrophoretically separate nucleic acids but polyacrylamide gel electrophoresis (PAGE) is also harnessed to separate relatively small nucleic acids (e.g., a few base pairs to several thousand base pairs). PAGE of nucleic acids offers advantages of higher resolution of bands and being suitable for more sensitive detection methods over agarose gel electrophoresis. Nevertheless, no matter which method is used—agarose or PAGE—it is very challenging to efficiently recover separated nucleic acids after electrophoresis, due to their gigantic size.

SUMMARY

This application relates to a degradable polyacrylamide gel and to a method of separating and isolating at least one macromolecule from a biological sample using the degradable polyacrylamide gel. The degradable polyacrylamide gel can include a polyacrylamide that is cross-linked with at least one degradable cross-linker. The degradable cross-linker can include a ketal or acetal group having the formula (I):

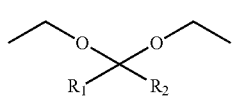

wherein $R_1$ and $R_2$ are the same or different and are hydrogen, an alkyl, or a substituted alkyl.

In another aspect of the application, the at least one degradable cross-linker can include the formula (II):

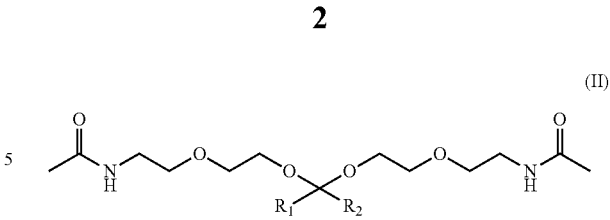

wherein $R_1$ and $R_2$ are the same or different and are hydrogen, an alkyl, or a substituted alkyl. The alkyl can be a $C_1$-$C_5$ alkyl.

The application also relates to a method of separating and isolating at least one polynucleotide, polynucleotide complex, virus, polynucleotide-protein complex, or protein complex from a biological sample. The method includes providing an electrophoresis device that includes a degradable polyacrylamide gel. The degradable polyacrylamide gel can include a polyacrylamide that is cross-linked with at least one degradable cross-linker. The degradable cross-linker can include a ketal or acetal group having the formula (I):

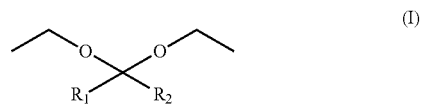

wherein $R_1$ and $R_2$ are the same or different and are hydrogen, an alkyl, or a substituted alkyl. At least one biological sample including at least one polynucleotide, polynucleotide complex, virus, polynucleotide-protein complex, or protein complex can be loaded into the degradable polyacrylamide gel. Electrophoresis can then performed on the degradable polyacrylamide gel loaded with the sample to separate the at least one polynucleotide, polynucleotide complex, virus, polynucleotide-protein complex, or protein complex in the degradable polyacrylamide gel.

In an aspect of the application, the degradable polyacrylamide gel can be stained to visualize the at least one polynucleotide, polynucleotide complex, virus, polynucleotide-protein complex, or protein complex contained therein. In another aspect of the application, at least one fraction containing the at least one polynucleotide, polynucleotide complex, virus polynucleotide-protein complex, or protein complex can be excised from the degradable polyacrylamide gel and the at least one excised fraction can be at least partially solubilized to isolate the at least one polynucleotide, polynucleotide complex, polynucleotide-protein complex, or protein complex.

The application also relates to a method of determining the functional activity of at least one polynucleotide, polynucleotide complex, virus, polynucleotide-protein complex, protein or protein complex in a cell. The method includes obtaining a biological sample comprising at least one polynucleotide, polynucleotide complex, virus, polynucleotide-protein complex, protein or protein complex. The biological sample including the at least one polynucleotide, polynucleotide complex, virus, polynucleotide-protein complex, or protein complex can be loaded into a degradable polyacrylamide gel of an electrophoresis device. The degradable polyacrylamide gel can include a polyacrylamide that is cross-linked with at least one degradable cross-linker. The degradable cross-linker can include a ketal or acetal group having the formula (I):

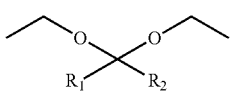

wherein $R_1$ and $R_2$ are the same or different and are hydrogen, an alkyl, or a substituted alkyl. Electrophoresis can then performed on the degradable polyacrylamide gel loaded with the sample to separate the at least one polynucleotide, polynucleotide complex, virus, polynucleotide-protein complex, or protein complex in the degradable polyacrylamide gel. At least one fraction containing the at least one polynucleotide, polynucleotide complex, virus, polynucleotide-protein complex, protein or protein complex can be excised from the degradable polyacrylamide gel and the at least on excised fraction can be at least partially solubilized to isolate the at least one polynucleotide, polynucleotide complex, virus polynucleotide-protein complex, or protein complex. The isolated polynucleotide, polynucleotide complex, virus, polynucleotide-protein complex, protein and/or protein complex can then be administered to a cell. The functional activity of the polynucleotide, polynucleotide complex, polynucleotide-protein complex, virus, protein and/or protein complex can then be measured in the cell.

In another aspect of the application, the at least one degradable cross-linker can include the formula (II):

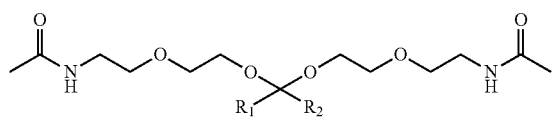

wherein $R_1$ and $R_2$ are the same or different and are hydrogen, an alkyl, or a substituted alkyl. The alkyl can be a $C_1$-$C_5$ alkyl.

In another aspect of the application, the isolated polynucleotide, virus, or polynucleotide complex can be administered to the cells by transfecting the cells with the polynucleotide or polynucleotide complex. The protein, protein complex or protein-polypeptide complex can be administered to the cells by nano-injection.

BRIEF DESCRIPTION OF THE DRAWINGS

The foregoing and other features of the present invention will become apparent to those skilled in the art to which the present application relates upon reading the following description with reference to the accompanying drawings, in which.

DETAILED DESCRIPTION

Figure 1:
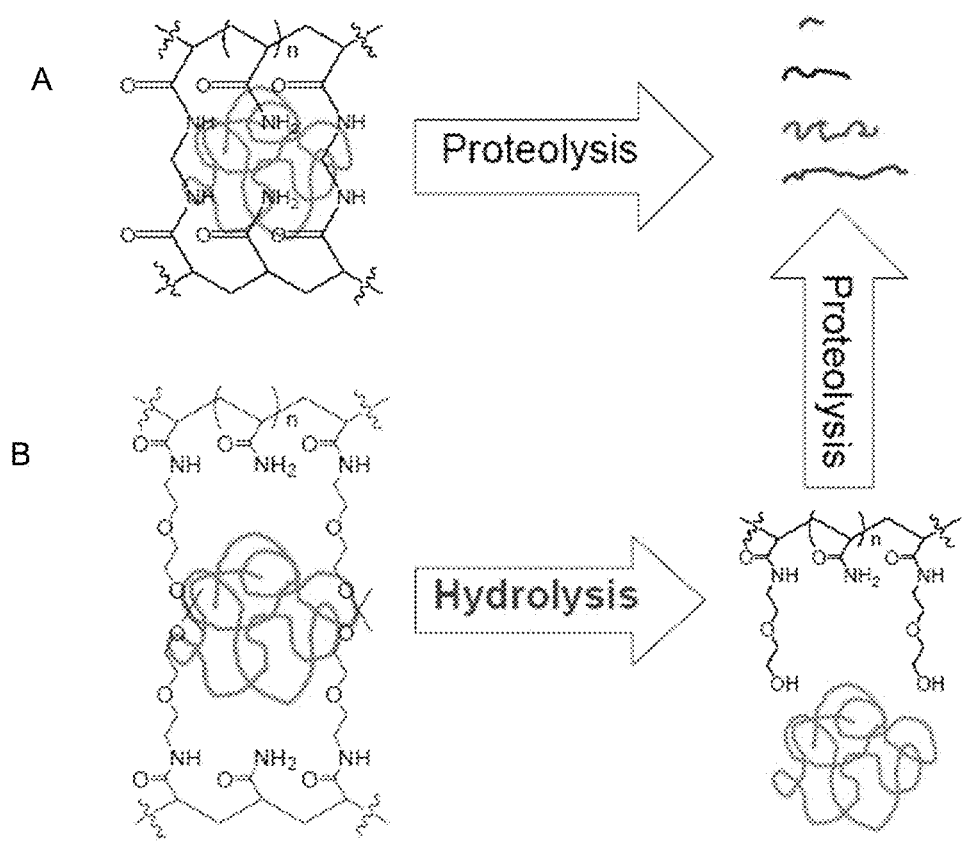
FIGS. 1A-B are a schematic representation comparing polyacrylamide gel structure and function of the prior art (FIG. 1A) and the present invention (FIG. 1B)

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present application pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the application.

As used herein, the term "ketal" refers to a functional group bearing two alkyl groups and two alkoxy groups on one carbon atom. Ketals typically have the formula $R_2C(OR)_2$ and are produced in the acid-catalyzed alcoholysis of a ketone or a hemiketal.

As used herein, the term "acetal" refers to a functional group bearing an alkyl group, a hydrogen atom, and two alkoxy groups on one carbon atom. Acetals typically have the formula $RCH(OR)_2$ and are produced in the acid-catalyzed alcoholysis of an aldehyde or a hemiacetal.

As used herein, the terms "alkyl" or "substituted alkyl" refer to a straight chain or branched chain hydrocarbon radical having from about 1 to about 10 carbon atoms. Examples of such alkyls or substituted alkyls include methyl, ethyl, n-propyl, isopropyl, n-butyl, isobutyl, s-butyl, t-butyl, pentyl, neopentyl, hexyl, isohexyl, and the like.

As used herein, the term "macromolecule" refers to any molecule having a molecular weight from the hundreds up to the millions. Macromolecules can include polypeptides, proteins, polynucleotides, nucleic acids, viruses, plasmids, viral vectors, polysaccharides, carbohydrates, and other such molecules including but not limited to those that are generally synthesized by biological organisms as well as those that can be prepared synthetically or using recombinant molecular biology methods.

As used herein, the term "electrophoresis" refers to the movement of charged macromolecules suspended in a separation medium (e.g., polyacrylamide or agarose) under the influence of an applied electric field. If the electric field is applied between electrodes in a cell, the macromolecules may migrate, depending on their polarity, to either a cathode or anode while the separation medium remains substantially stationary. When a coincident voltage is applied to the electrodes, the macromolecules in the separation medium may migrate under the influence of the electric field to the anode or cathode having a polarity opposite from their own.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term also encompasses nucleic acids, i.e., oligonucleotides, containing known analogues of natural nucleotides. The term also encompasses nucleic acid-like structures with synthetic backbones.

As used herein, the term "polypeptide" refers to an oligopeptide, peptide, polypeptide, or protein sequence, or to a fragment, portion, or subunit of any of these, and to naturally occurring or synthetic molecules. The terms "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

This application generally relates to gel electrophoresis, and more particularly to a degradable polyacrylamide gel for separating or analyzing at least one macromolecule in a sample. The degradable polyacrylamide gel allows highly efficient isolation and recovery of structurally intact macromolecules, such as polynucleotides, polynucleotide complexes, viruses, polynucleotide-protein complexes, proteins, or protein complexes, from biological samples and to the use of such isolated macromolecules in diagnostic and therapeutic applications.

In one aspect of the application, the degradable polyacrylamide gel includes a polyacrylamide that is cross-linked with at least one degradable cross-linker. The at least one degradable cross-linker can include a ketal or acetal group that is hydrolysable when contacted with an acidic solution. The ketal or acetal group can include the formula (I):

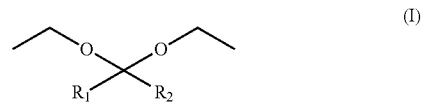

(I)

wherein $R_1$ and $R_2$ may be the same or different, and may include hydrogen, an alkyl, or a substituted alkyl. In one example, $R_1$ and $R_2$ can be methyl groups.

Alternatively or additionally, the at least one degradable cross-linker may comprise a ketal or acetal group having the formula (II):

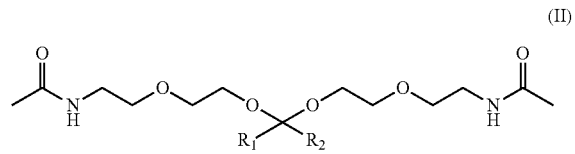

(II)

wherein $R_1$ and $R_2$ are the same or different and are hydrogen, an alkyl, or a substituted alkyl. In one example, alkyl can be a $C_1$-$C_5$ alkyl. In another example, $R_1$ and $R_2$ can be methyl groups.

The ketal or acetal groups of the degradable polyacrylamide gels of the application can be readily hydrolyzed after separation and/or isolation of the macromolecules. Hydrolysis of the degradable cross-linker allows release of structurally intact macromolecules (e.g., polynucleotides, polynucleotide complexes, viruses, polynucleotide-protein complexes, proteins, or protein complexes) from the polyacrylamide matrix (FIG. 1B) in contrast to conventional polyacrylamide gels that prevent or hinder release of intact macromolecules (e.g., polynucleotides, polynucleotide complexes, viruses, polynucleotide-protein complexes, proteins, or protein complexes) upon degradation of the polyacrylamide gel (FIG.

1A). The degradable polyacrylamide gel, thus, provides an ideal suspending medium for the separation or analysis of macromolecules.

The degradable polyacrylamide gel can be prepared by cross-linking a polyacrylamide with at least one degradable cross-linker. In one example, the at least one degradable cross-linker can have the formula (III):

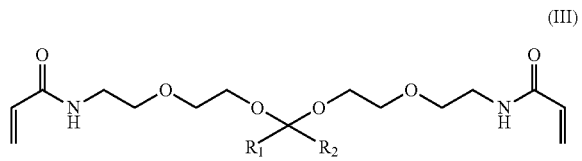

(III)

wherein $R_1$ and $R_2$ may be the same or different. $R_1$ and $R_2$ may comprise hydrogen, an alkyl, or a substituted alkyl. In one example, $R_1$ and $R_2$ can be methyl groups.

The degradable polyacrylamide gel can be formed by the co-polymerization of acrylamide monomers and the at least one cross-linker in an appropriate buffer having a pH buffering (e.g., capacity between about 3.0 and 11.0).

Examples of buffers that can be used include tris-borate-EDTA (TBE), trishydroxyaminomethane (TRIS, THAM), ethylamine (EA), diethylamine (DEA), ethanolamine (EOA), (3-[cyclohexylamino]-2-hydroxy-1-propane sulfonic acid (CAPSO), (2-[N-cyclohexylamino]ethane sulfonic acid (CHES), (3-[1,1-dimethyl-2-hydroxy ethyl)amino]-2-hydroxypropanesulfonic acid) (AMPSO), (N,N-bis[2-hydroxyethyl)glycine (BICINE), (3-[N,N-bis(2 hydroxyethyl)amino]-2-hydroxy propane sulfonic acid) (DIPSO), (N4-[2-hydroxyethyl]piperazine-N1-[2-ethanesulfonic acid (HEPES), (N,N-bis[2-hydroxyethyl]glycine) (BICINE), triethano-lamine (TEA), (N-tris[hydroxymethyl]methyl glycine (TRICINE), (N-tris[hydroxymethyl]-3-aminopropane sulfonic acid) (TAPS), (N-[2hydroxyethyl]piperazine-N1-[3-propane sulfonic acid] (EPPS), (N-[2-hydroxyethyl]piperazine-N1-[2-hydroxy propane sulfonic acid] (HEPPSO), and (piperazine-N,N1-bis[hydroxy propane sulfonic acid] (POPSO).

The acrylamide monomers can polymerize into long chains, which are cross-linked at intervals by the at least one degradable cross-linker, thereby forming the degradable polyacrylamide gel. The porosity of the degradable polyacrylamide gel can be altered by changing the percentage of acrylamide used and/or the amount of the at least one cross-linker present. For example, a higher percentage of acrylamide will yield a denser gel with better ability to separate smaller macromolecules. In contrast, a lower percentage of acrylamide will yield a more porous gel that generally favors the separation of larger macromolecules.

By way of example, a degradable polyacrylamide gel can be prepared by dissolving about 0.95 g of acrylamide and about 0.05 g of the at least one degradable cross-linker in about 2.5 mL of TBE buffer. To prepare a cross-linked gel of about 10% (w/w), about 2.5 mL of the dissolved solution may be mixed with about 7.5 mL of TBE buffer. Next, about 10 mg of ammonium persulfate may be added and mixed well for about 5 minutes. About 4 µL of TEMED may be added to the mixture, which may then be incubated at about room temperature for about 2 hours.

The degradable polyacrylamide gels so formed can be used in any type of gel electrophoresis device to separate and isolate macromolecules. For example, degradable polyacrylamide gels can be used to form slab gels, such as those used in horizontal electrophoresis, or used in capillary electrophoresis. Alternatively, degradable polyacrylamide gels can be configured for use in high-throughput protein separations. Electrophoresis techniques are well known in the art and can be readily adapted by one of ordinary skill in the art for use with the degradable polyacrylamide gels described herein.

Figure 2:
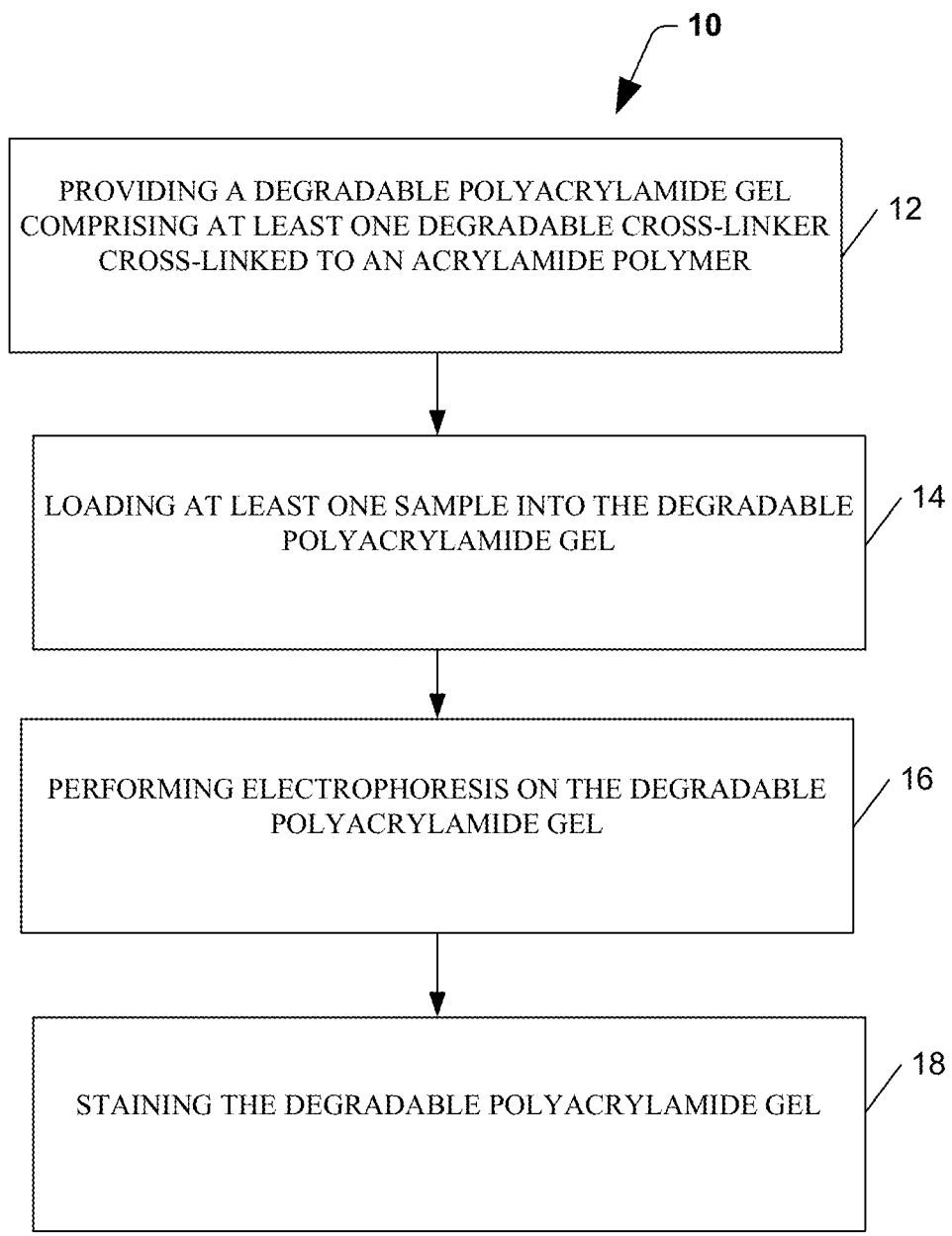
FIG. 2 is a flow diagram illustrating a method for separating or analyzing at least one macromolecule in a sample.

FIG. 2 is a flow diagram illustrating a method 10 of separating or analyzing at least one macromolecule in a sample using an electrophoresis device that includes a degradable polyacrylamide gel described herein. The method can be used with a wide range of sample types. Essentially any macromolecule-containing sample can be utilized with the methods described herein. The samples can contain a relatively small number of macromolecules or can contain a large number of macromolecules, such as all the polynucleotides, polynucleotide complexes, polynucleotide-protein complexes, proteins or protein complexes within a cell or tissue sample. The macromolecules can include, for example, at least one polynucleotide, polynucleotide complex, virus, polynucleotide-protein complex, protein or protein complex.

Samples can be obtained from any organism or can be mixtures of synthetically prepared macromolecules or combinations thereof. For example, samples can be obtained from microorganisms (e.g., viruses, bacteria and fungi), animals (e.g., cows, pigs, horses, sheep, dogs and cats), hominoids (e.g., humans, chimpanzees, and monkeys) and plants. The samples can also come from tissues, tissue homogenates, or fluids of an organism or cell cultures. For example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components.

Sample preparation for various electrophoresis techniques is known in the art. If a sample contains cellular debris or other non-protein material that might interfere with separation during electrophoresis such material can be removed using any of a variety of known separation techniques, including forcibly exuding the sample through sieve material, filtration and centrifugation. Samples whose ionic strength is particularly high can be desalted using established techniques, such as dialysis, dilution, and re-concentration.

In the method 10, at 12, a degradable polyacrylamide gel can be provided. The degradable polyacrylamid gel can be prepared as described above. For example, an acrylamide polymer may be cross-linked with at least one degradable cross-linker in an appropriate buffer solution. The at least one degradable cross-linker may include a ketal or acetal group having the formula (I):

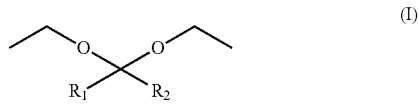

(I)

wherein $R_1$ and $R_2$ are the same or different and are hydrogen, an alkyl, or a substituted alkyl.

Alternatively or additionally, the at least one degradable cross-linker may comprise a ketal or acetal group having the formula (II):

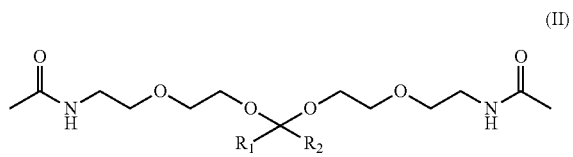

(II)

wherein $R_1$ and $R_2$ are the same or different and are hydrogen, an alkyl, or a substituted alkyl.

Polymerization and cross-linking of the acrylamide with the at least one degradable cross-linker can be initiated by providing a catalyst (e.g., TEMED) and an initiator (e.g., ammonium persulfate) in a solution containing the acrylamide and the cross-linker. The solution can then be quickly transferred to an electrophoresis chamber where polymerization takes place. The polymerization transforms the solution into a firm gel, typically within about an hour. A slot-forming gel comb may then be set in place at one end of the gel.

After polymerizing the degradable polyacrylamide gel, the chamber may be placed in an electrophoresis cell (i.e., where electrophoresis may be performed). In continuous electrophoresis, buffer solution of identical ionic strength, composition and pH as the buffer solution incorporated into the gel during polymerization may be added to each buffer reservoir. In discontinuous electrophoresis, a different buffer solution (but generally having a counter ion common with the buffer polymerized in the gel) may be added to one of the reservoirs. Electrodes in each reservoir may be connected to a direct current power supply.

At this point a complete electric circuit exists and the degradable polyacrylamide gel can be used for application of the at least one sample. At 14, the at least one sample may be loaded into the degradable polyacrylamide gel using, for example, a pipet or other similar device. It will be appreciated that the at least one sample may comprise any number of components needed to properly perform electrophoresis. Such additional components are known in the art and can include, for example, different running buffers, dyes, markers (e.g., protein or DNA size markers), and the like. It should be appreciated that prior to loading the at least one sample, it may be desirable to apply potential to the circuit by means of the power supply. This may be done to cause migration of residual ammonium persulfate and other charged residues of the gel formation process away from the sample application region of the degradable polyacrylamide gel.

After the at least one sample has been loaded into the degradable polyacrylamide gel, electrophoresis may be performed at 16. An appropriate voltage and current may be established by means of the direct current power supply for a time sufficient to complete the resolution of the at least one sample. At 18, several known techniques may then be used to resolve or identify the presence of the at least one sample. Such techniques generally include staining with zinc or copper, Coomassie blue, silver, fluorescent stains (e.g., SYPRO ruby), and the like.

In an example of the method 10, a degradable polyacrylamide gel may be used to analyze or separate a macromolecule, such as a polypeptide, using electrophoresis. About 10 µL, of a protein loading buffer and about 10 µL, of about 30% of a particular polypeptide may be combined to form samples. The samples may then be loaded into at least one well of the degradable polyacrylamide gel. Electrophoresis may be run at about 4° C. in 150 V for about 60 minutes. After electrophoresis, the degradable polyacrylamide gel may be separated from the electrophoresis apparatus and washed two or more times with de-ionized water. The degradable polyacrylamide gel may then be stained for about 30 minutes at 4° C. with Coomassie blue solution after adjustment to a pH of about 5.0. The degradable polyacrylamide gel may then be destained with de-ionized water for about one hour at about 4° C. with mild shaking.

Figure 3:
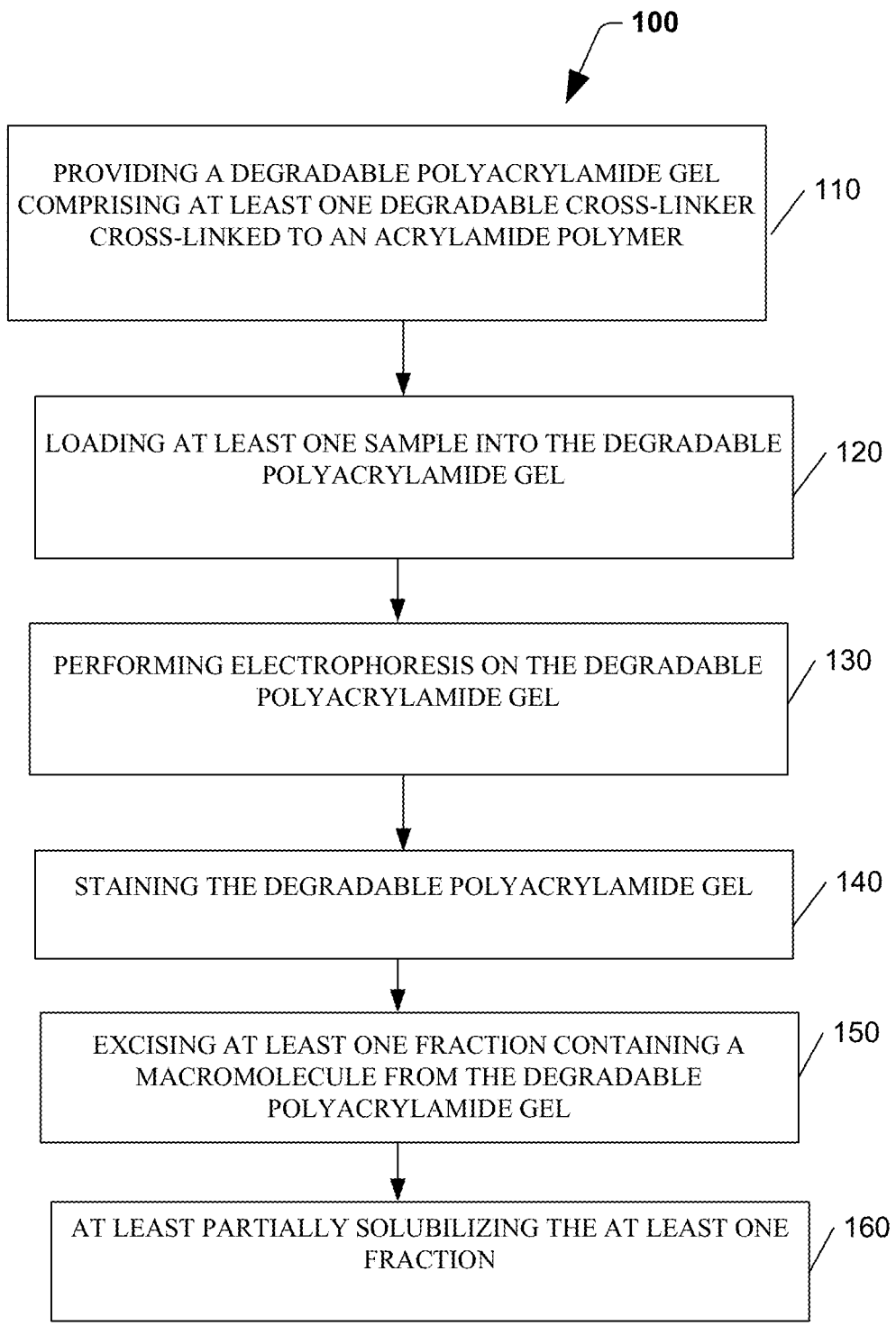
FIG. 3 is a flow diagram illustrating another method for separating or analyzing at least one macromolecule in a sample.

FIG. 3 is a flow diagram illustrating another aspect of the application. In FIG. 3, a method 100 is provided for separating or analyzing at least one macromolecule in a sample. In the method 100, a degradable polyacrylamide gel may be prepared at 110 as described above. At 120, at least one sample may then be loaded into the degradable polyacrylamide gel and electrophoresis performed at 130 (as described above). As also described above, the degradable polyacrylamide gel may be stained at 140.

After electrophoresis, a fraction or band of interest may be excised from the degradable polyacrlamide gel at 150. The fraction of interest may comprise the at least one macromolecule, and may be determined by comparing the position of the fraction on the gel with the position of a particular control marker (also on the gel). Techniques for excising fractions from polyacrylamide gels are known in the art. For example, a fraction of interest may be excised from a gel using a razor blade or other similar tool. The fraction of interest may be carefully excised such that the amount of any excess polyacrylamide removed is minimized.

After excising the fraction of interest, the fraction may be at least partially solubilized at 160 with a solubilizing agent. The solubilizing agent can include any agent that facilitates hydrolysis of the ketal or acetal group of the at least one degradable cross-linker. For instance, a mild organic acid, such as acetic acid, may be used to hydrolyze or degrade the fraction. As shown in FIG. 1B, addition of the solubilizing agent hydrolyzes the ketal or acetal group of the at least one cross-linker and thereby allows release of a structurally intact macromolecule from the degradable polyacrylamide gel.

In one example of the method 100, a fraction or band of interest may be cut from a degradable polyacrylamide gel after electrophoresis. The extracted band may be placed in a 15 mL centrifuge tube. About 4 mL of acetic acid buffer (about 300 mM acetic acid in de-ionized water) having a pH of about 5.0 may then be added into the centrifuge tube. The centrifuge tube may then be incubated at about 37° C. for about 5 hours with shaking. After incubation, about 0.4 mL of acetonitrile may be added to the centrifuge tube. The centrifuge tube may then be incubated for about 10 minutes at room temperature with occasional shaking. After incubation, about 3.6 mL of acetonitrile may be added to the mixture and vigorously shaken, followed by incubation at about room temperature for about one hour. Next, the precipitated pellet may be removed after centrifugation at about 4200 rpm for about 15 minutes. After centrifugation, the supernatant may be removed from the centrifuge tube and transferred into a 50 mL centrifuge tube. About 10 mL of acetonitrile may then be added to the 50 mL centrifuge tube. The 50 mL centrifuge tube may be shaken and incubated at about room temperature for about 1 hour. The 50 mL tube may then be centrifuged at about 4200 rpm for about 15 minutes. After centrifugation, the resultant pellet, which contains at least one macromolecule, may be re-suspended in about 10 µL of TBE buffer and analyzed as desired.

Degradable polyacrylamide gels of the present invention may find use in any number of known electrophoresis assays.

For example, degradable polyacrylamide gels can be used for high throughput electrophoresis. The ease of preparation, predictability, stability, and good resolution make the gels of the present invention ideal for high throughput protein or nucleic acid electrophoresis.

Alternatively, a degradable polyacrylamide gel of the present invention may be used to carry out two-dimensional gel electrophoresis. Two-dimensional gel electrophoresis separates macromolecules in two steps, based on two independent properties: (1) the first-dimension is isoelectric focusing, which separates proteins according to their isoelectric points (pI); and (2) the second-dimension is SDS-PAGE, which separates macromolecules according to their molecular weights. The procedure generally involves placing a sample in the gel with a pH gradient and then applying a potential difference across it. In the electrical field, the protein can migrate along the pH gradient until it carries no overall charge. This location of the protein constitutes the apparent pI of the protein. The second step is performed in slab SDS-PAGE.

Because the methods of the macromolecules can provide structurally intact macromolecules, it should be appreciated that resolved macromolecules, e.g., polynucleotides, polynucleotide complexes, viruses, polynucleotide-protein complexes, proteins or protein complexes, can be further analyzed by non-electrophoretic methods. Examples of such methods include infrared spectroscopy, nuclear magnetic resonance spectroscopy, UV/VIS spectroscopy, and complete or partial sequencing. Coupling the current electrophretic-based methods to various mass spectroscopy (MS) methods is one specific example of further analysis that can be conducted. A variety of mass spectral techniques can be utilized including, for example, several MS/MS methods and electrospray-time of flight MS methods. Such methods can be used to determine at least a partial sequence for polynucleotides, polynucleotide complexes, polynucleotide-protein complexes, proteins or protein complexes resolved by the electrophoretic methods.

Another aspect of application relates to a method of determining the functional activity of at least one polynucleotide, polynucleotide complex, polynucleotide-protein complex, protein or protein complex in a cell a method of determining the functional activity of at least one polynucleotide, polynucleotide complex, virus, polynucleotide-protein complex, protein or protein complex in a cell. The method includes obtaining a biological sample comprising at least one polynucleotide, polynucleotide complex, virus, polynucleotide-protein complex, protein or protein complex. The biological sample including the at least one polynucleotide, polynucleotide complex, virus, polynucleotide-protein complex, or protein complex can be loaded into a degradable polyacrylamide gel of an electrophoresis device. The degradable polyacrylamide gel can include a polyacrylamide that is cross-linked with at least one degradable cross-linker. The degradable cross-linker can include a ketal or acetal group having the formula (I):

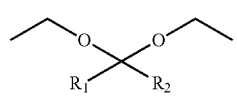

(I)

wherein $R_1$ and $R_2$ are the same or different and are hydrogen, an alkyl, or a substituted alkyl.

By way of example, the at least one degradable cross-linker can include the formula (II):

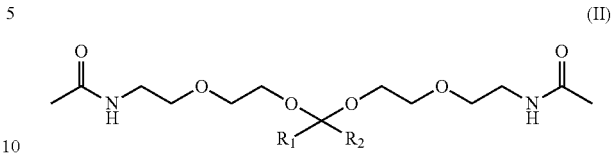

(II)

wherein $R_1$ and $R_2$ are the same or different and are hydrogen, an alkyl, or a substituted alkyl. The alkyl can be a $C_1$-$C_5$ alkyl.

Electrophoresis can then performed on the degradable polyacrylamide gel loaded with the sample to separate the at least one polynucleotide, polynucleotide complex, virus, polynucleotide-protein complex, or protein complex in the degradable polyacrylamide gel. An appropriate voltage and current may be established by means of the direct current power supply for a time sufficient to complete the resolution of the at least one sample.

At least one fraction containing the at least one polynucleotide, polynucleotide complex, virus, polynucleotide-protein complex, protein or protein complex can be excised from the degradable polyacrylamide gel. The fraction of interest may comprise the at least one macromolecule, and may be determined by comparing the position of the fraction on the gel with the position of a particular control marker (also on the gel). Techniques for excising fractions from polyacrylamide gels are known in the art.

The at least on excised fraction can then be at least partially solubilized to isolate the at least one polynucleotide, polynucleotide complex, virus polynucleotide-protein complex, or protein complex. The solubilizing agent can include any agent that facilitates hydrolysis of the ketal or acetal group of the at least one degradable cross-linker. For instance, a mild organic acid, such as acetic acid, may be used to hydrolyze or degrade the fraction.

The isolated polynucleotide, polynucleotide complex, virus, polynucleotide-protein complex, protein and/or protein complex can then be administered to a cell. For example, the isolated polynucleotide, virus, or polynucleotide complex can be administered to the cells by transfecting the cells with the polynucleotide or polynucleotide complex. Alternatively or additionally, the protein, protein complex or protein-polypeptide complex can administered to the cells by nano-injection.

The functional activity of the polynucleotide, polynucleotide complex, polynucleotide-protein complex, virus, protein and/or protein complex can then be measured in the cell. The functional activity of the polynucleotide, polynucleotide complex, polynucleotide-protein complex, virus, protein and/or protein complex can be meaured in a variety of ways. Examples of how functional activity can be measured are provided below and can include, but are not limited to: (1) subcellular localization of polynucleotide, polynucleotide complex, polynucleotide-protein complex, virus, protein and/or protein complex (e.g., immunofluorescence analysis in permeabilized cells; ultrastructural analysis in cells with specific antibodies and electron microscopy; and Western blot analysis of polynucleotide, polynucleotide complex, polynucleotide-protein complex, virus, protein and/or protein complex in cell membrane subfractions); (2) determination of polynucleotide, polynucleotide complex, polynucleotide-protein complex, virus, protein and/or protein complex interactions (e.g., immunoprecipitation of polynucleotide, polynucleotide complex, polynucleotide-protein complex, virus, protein and/or protein complex(s) from cell extract and gel analysis of precipitate; and immobilization of polynucleotide, polynucleotide complex, polynucleotide-protein complex, virus, protein and/or protein complex to study in vitro assembly of a multiprotein complex); (3) functional assay of polynucleotide, polynucleotide complex, polynucleotide-protein complex, virus, protein and/or protein complex (e.g., immunoprecipitation of polynucleotide, polynucleotide complex, polynucleotide-protein complex, virus, protein and/or protein complex from cell extract and activity assay, such as phosphorylation of immunoprecipitate; and Western blot detection of polynucleotide, polynucleotide complex, polynucleotide-protein complex, virus, protein and/or protein complex(s) in cellular extracts under varying conditions, such as activation or suppression of a cell function); (4) tracking movement of polynucleotide, polynucleotide complex, polynucleotide-protein complex, virus, protein and/or protein complex within a cell (e.g., immunoprecipitation of polynucleotide, polynucleotide complex, polynucleotide-protein complex, virus, protein and/or protein complex(s) from cell extract after pulse-chase labeling; immunofluorescence analysis in intact cell membranes; localization in cells with specific antibody and electron microscopy; and localization in cells with confocal immunofluorescence microscopy); and (5) characterization of new proteins expressed (e.g., Western blot analysis of protein(s) expressed by transfected cell lines; purification of protein(s) from cell extract by affinity chromatography; and immunoprecipitation of protein(s) from cell extract and gel analysis of subunit structure).

The following examples are for the purpose of illustration only and are not intended to limit the scope of the claims, which are appended hereto.

EXAMPLE 1

In the following example, we describe a novel approach to extract intact proteins keeping the quaternary structure of proteins using a degradable gel in acidic condition prepared by acetal crosslinker instead of bis-acrylamide. The hydrolysis of acetal crosslinker was depicted in FIG. 1. Mouse IgG1 monoclonal antibody of 150 kDa was electrophoresed without any reducing agents including SDS (sodium dodecylsulfate) and the recovered amount of biologically active IgG1 was quantified using an ELISA (enzyme-linked immunosorbent assay) kit after hydrolysis of gel in acidic solution.

Native Gel Electrophoresis

Different concentration of degradable gels (6%, 8%, 10%, and 12%) with 5 wt % acetal crosslinker were prepared and run under 150 V for 80 min after 2.7 µg of IgG1 with glycerol and bromophenol blue dye was loaded in each well. Tris-CAPS buffer (60 mM of Tris and 40 mM of 3-(cyclohexylamino)-1-propanesulfonic acid) of pH 9.6 was used as a running buffer because pI value of antibody IgG1 was close to 8. Any reducing agents, even SDS, which can denature proteins, were not used. Gels were stained with acidic/silver nitrate, which allowed gel permeation with silver ions at acidic pH, followed by reduction to elemental metallic silver with formaldehyde at alkaline pH. As gel concentration was higher, protein moved downward more slowly and resolution (separation) was better, especially at low MW. In contrast, 6% gel showed poor resolution. For further study, 8% or 10% gel was selected since the resolution was good enough at least at high MW (150 kD of IgG1) even though the best resolution could be obtained when 8~12% gradient gel is run. Except for the top band, which is intact mAb IgG1, the rest of bands were considered as free heavy chain and light chain or partially assembled antibodies. Only top bands could be quantified by ELISA, and sharp middle bands and thick bottom bands did not show any specificity in mouse IgG1 ELISA. In order to optimize the crosslinking ratio, 8% gels with different amount of acetal crosslinker (2.5, 5, and 10 wt % of total monomer amount) were prepared. Use of either 5% or 10% of crosslinker in case of 8% gel showed good resolution.

Quantification of Released IgG1 from Gels Using ELISA

In order to quantify the amount of IgG1 released from hydrolyzed gels, ELISA (enzyme-linked immunosorbent assay) was conducted. Top bands (intact IgG1 of MW ~150 kDa) were carefully excised using a sharp scalpel. Each excised band was incubated in hydrolyzing solution for more than 2 hours at room temperature. After ELISA assay was done, UV absorbance at 450 nm was measured. Gompertz growth model was fitted using Matlab for wider working range and more accurate standard curve fitting. Concentration of IgG1 was calculated from absorbance based on Gompertz model and dilution factor was multiplied. Data points of concentration within the range of 7.8~250 ng/ml were averaged. Data showing too low absorbance was excluded because those could easily make erroneous results due to low sensitivity and also small error can be amplified because of large dilution factor multiplied. For comparison, released IgG1 amount measured by ELISA was divided by the original IgG1 amount loaded in a gel.

Investigation on IgG1 Release Using Different Hydrolyzing Solution

After running 8 and 10% gels with 5 wt % acetal crosslinker for 80 min under 150 V, half of a gel was stained with silver nitrate. Both top bands of silver stained and unstained gels were hydrolyzed overnight in 3 ml of three different solutions of pH 3, 5 mM formic acid, 5 mM formic acid with 10 vol % of 2-propanol, and 100 mM acetate buffer with gentle shaking. After three hours, all the gel pieces except for 12% gel were completely dissolved and liquidified even though silver stained gels were rather slowly hydrolyzed than unstained ones.

Figure 4A:
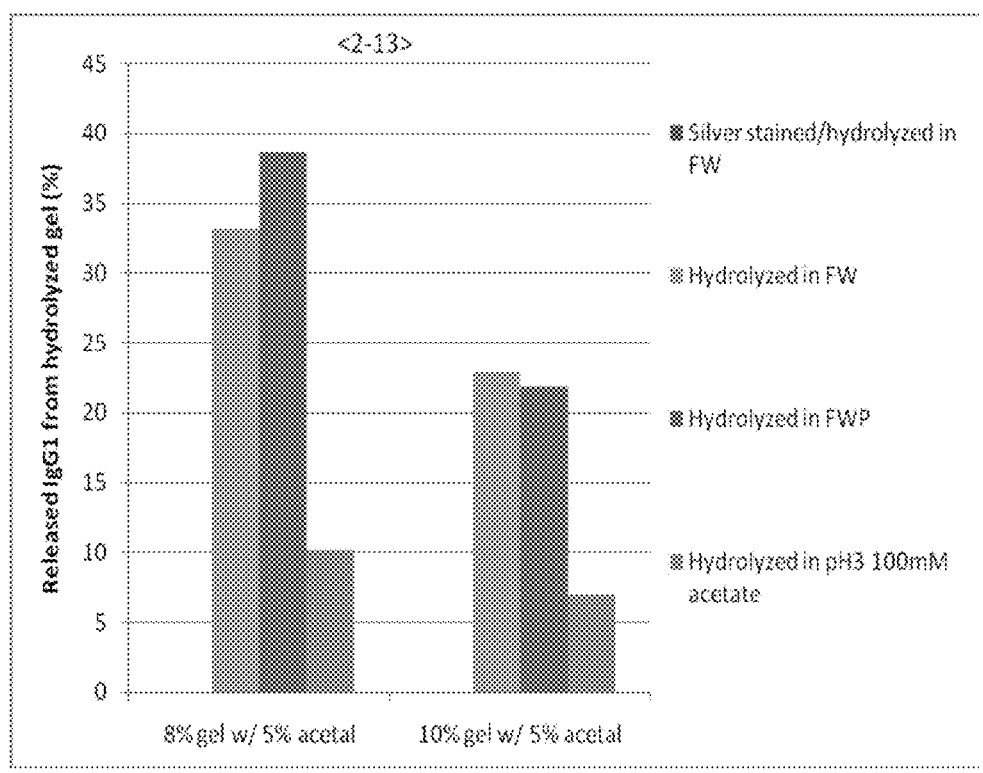
FIGS. 4A-C illustrate graphs showing released IgG1 from hydrolyzed gel in different hydrolyzing solution; 5 mM formic acid, 5 mM formic acid with 2-propanol (10 vol %) and 100 mM acetate buffer, was quantified using ELISA.
Figure 4B:
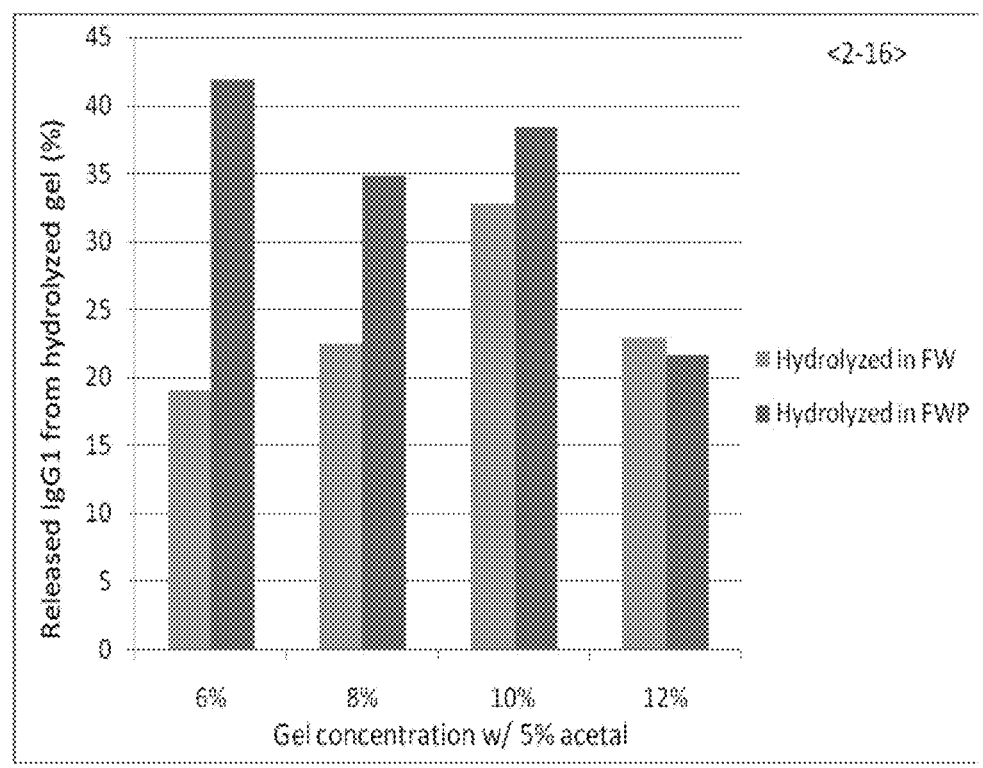
Figure 4C:
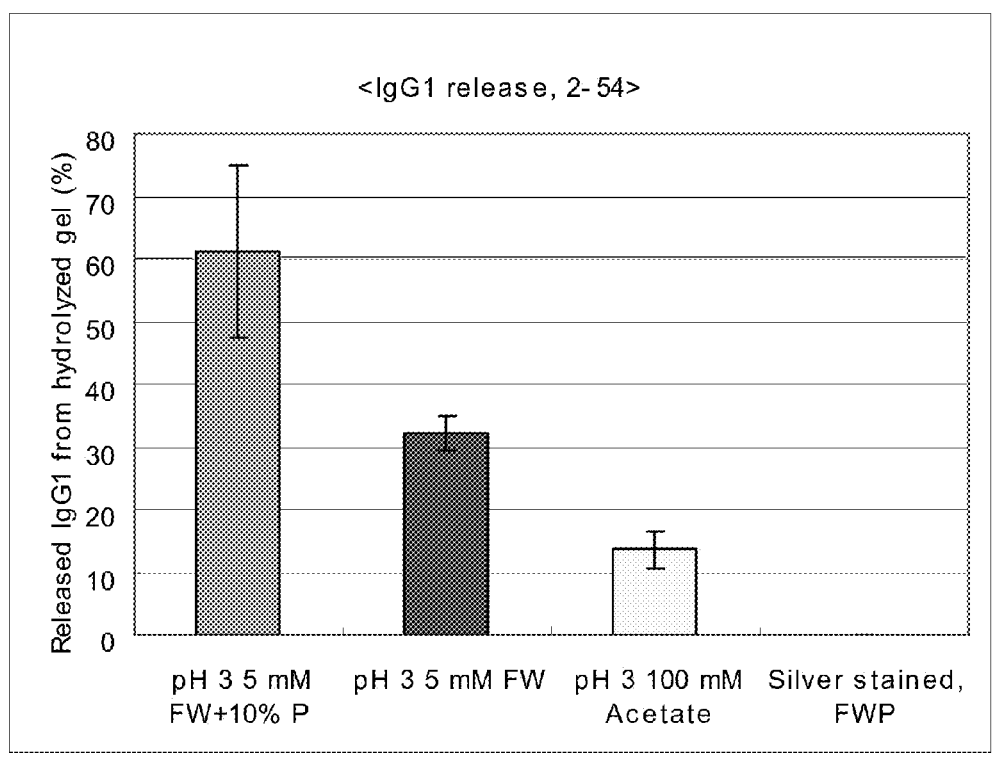

Referring to FIG. 4, silver stained gel piece did not show any active antibody release. It was supposed that formaldehyde used as a developing reagent in the process of silver staining affected on IgG1 activity, so that there was no color development in ELISA. Hydrolysis with FWP (90 vol % of 5 mM formic acid of pH 3 with 10 vol % of 2-propaneol) and FW (5 mM formic acid of pH 3) released up to 61% and 32% of IgG1, respectively, from 10% gel with 5% acetal crosslinker. Addition of 10% 2-propanol helped more release of IgG1. Formic acid with 2-propanol has been used as a RP-HPLC (reversed-phase high performance liquid chromatography) eluent since this combination had excellent protein-solubilizing properties, especially for large hydrophobic protein. IgG1 release was only 13% when hydrolyzed in 100 mM pH 3 acetate buffer. Probably smaller formate was more effective to extract protonated IgG1 at pH 3 than acetate. Optimal extraction efficiency was obtained with the formic acid/2-propanol (FWP) combination.

Figure 5A:
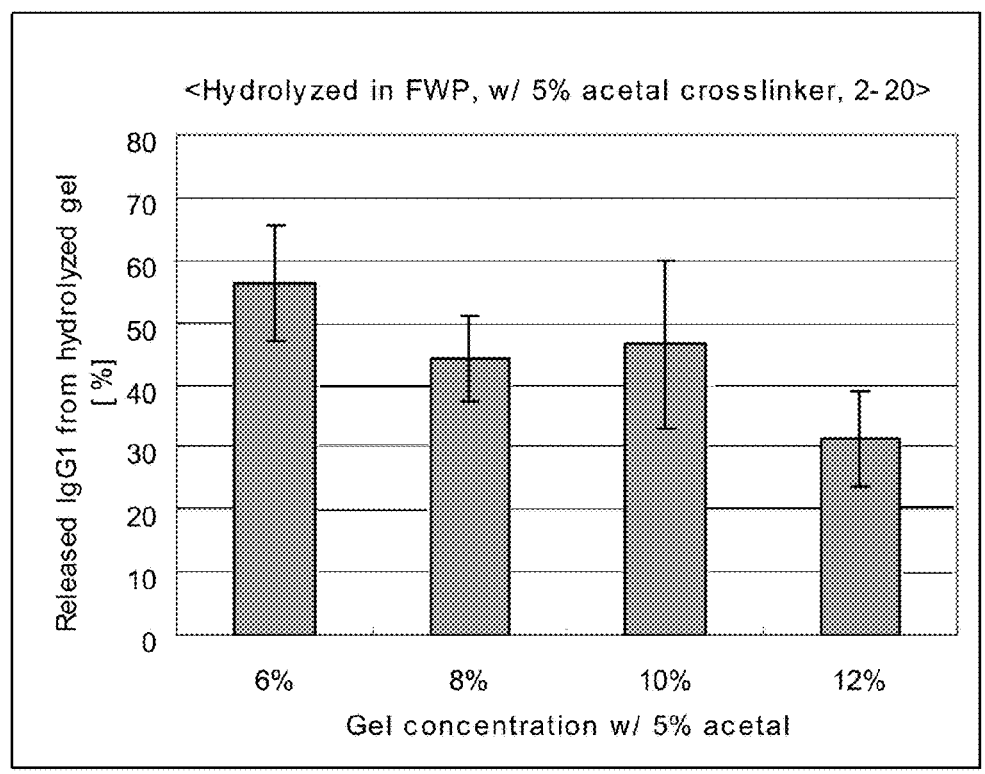
FIGS. 5A-B illustrate graphs showing that release of IgG1 was compared after hydrolysis of gels in FWP, 6, 8, 10, and 12% gels with 5 wt % of acetal crosslinker, and 8% gels with 2.5, 5, and 10 wt % of crosslinker.
Figure 5B:
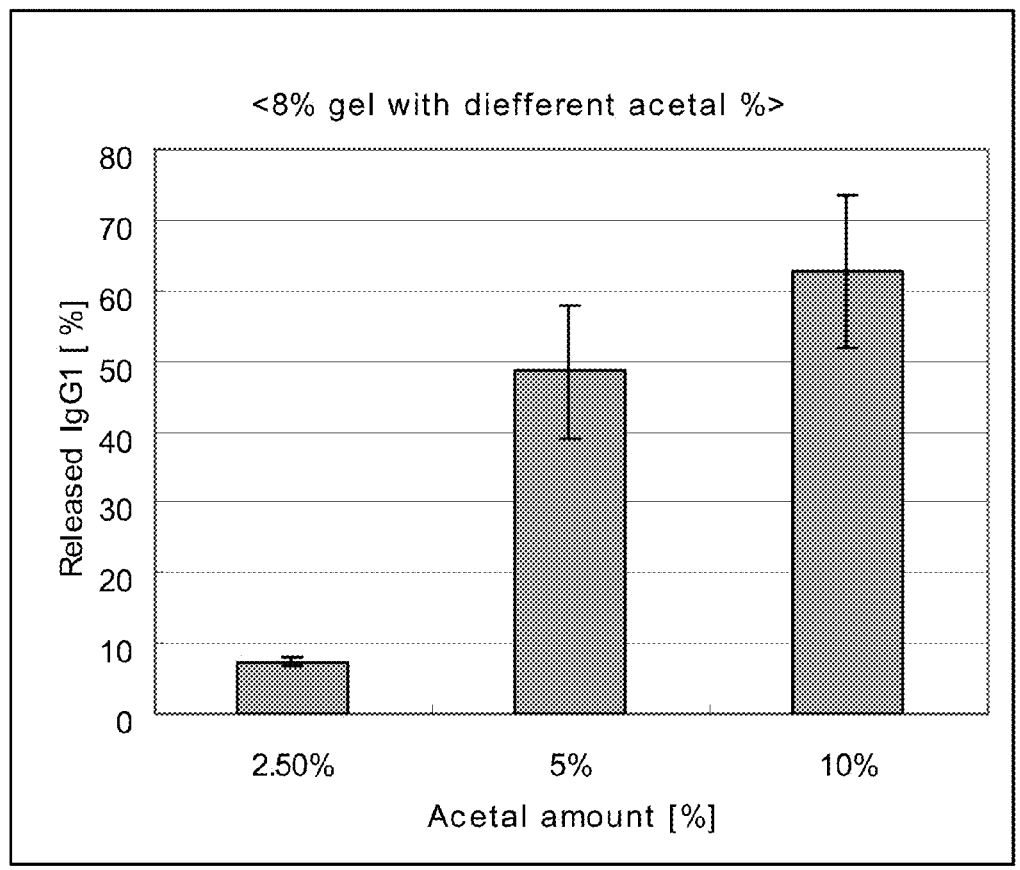

Investigation on IgG1 Release Depending on Gel Concentration and Crosslinker Amount Referring to FIG. 5, 6% gel showed the largest amount of release of IgG1, around 56%, and 12% gel showed the least, 32%, supposing that either only partial hydrolysis or high polymer concentration made very little space so that large IgG1 hardly came out from the polymer network. 8% gel with 2.5% crosslinker released IgG1 less than 10% and it could be explained that most of protein was diffused out through relatively big pore of polymer network while handling the gel (running, immersing in Tris/CAPS buffer during staining).
Comparison of IgG1 Release from Degradable Acetal and Nondegradable Bis-AA Gel At first, both polyacrylamide gels with acid-degradable acetal crosslinker and nondegradable typical bis-acrylamide were prepared with 8% of total gel concentration and 5 wt % of crosslinker. For better comparison, the same molar % of crosslinker should have been used rather than the same wt % even though the reactivity in polymerization of each crosslinker might be different. From the simple calculation, the same molar amount of acetal crosslinker with 2.67 wt % bis-acrylamide (commercialized) was 6 wt % of total monomer weight.

After incubation at room temperature for 30 min. 8% gel with 5% acetal was completely liquidified, in contrast, a gel piece made with bis-AA remained as it was.

Figure 6:
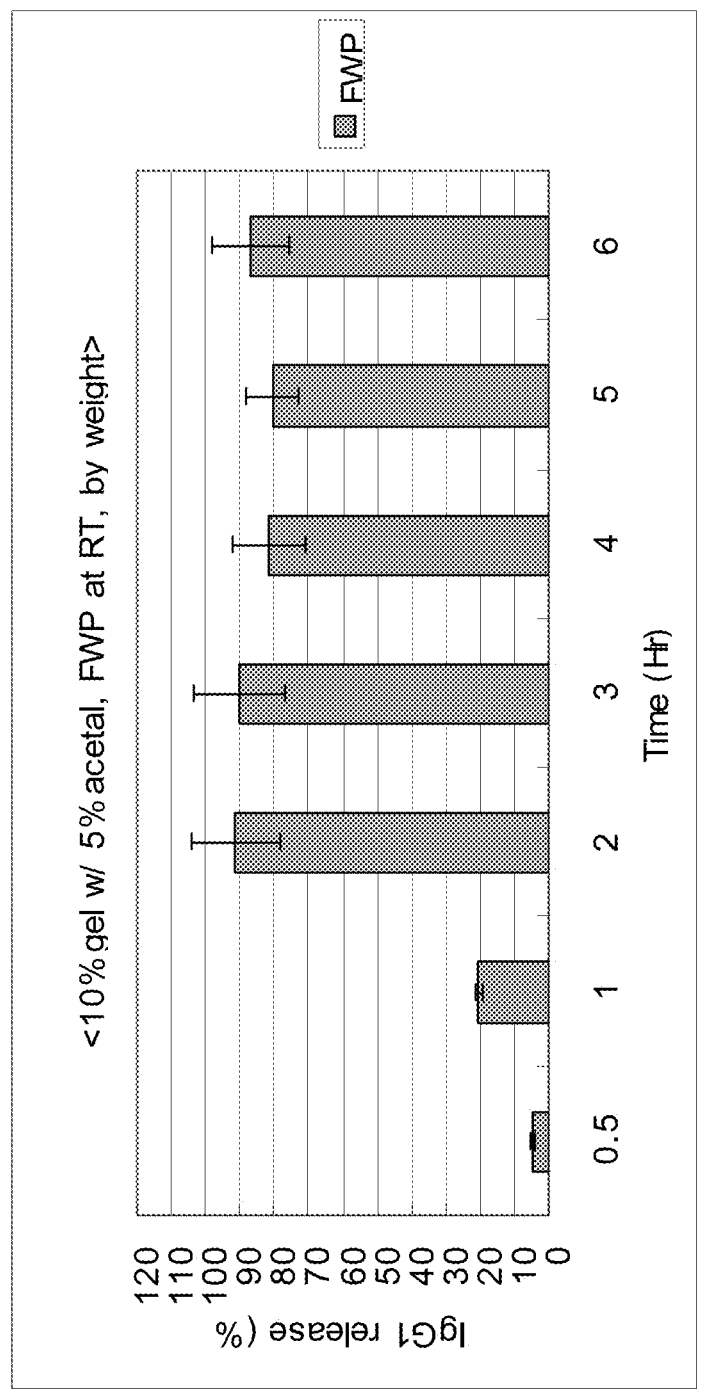
FIG. 6 illustrates graphs of an IgG1 release profile by time from 10% gel with 5 wt % acetal.

In order to find out the time point showing the maximum release of IgG1 when hydrolyzed in FWP solution, 10% gel with 5 wt % acetal was prepared and 600 µl of solution was taken at each hour after hydrolysis solution was added. Referring to FIG. 6, the maximum amount of IgG1 was released 2~3 hr after adding FWP solution.

To investigate how much IgG1 was released in water or Tris-CAPS buffer by simple diffusion and compare with release via hydrolysis using FWP for extended time up to 24 hr, the same experiment was done as above except 600 µl of sample was taken at 1, 2, 3, 6, 12, 24 hr time point after adding each solution and sample was incubated at 4° C. for 24 hr to prevent loss of IgG1 activity or degradation from storing in pH 3 solution at R.T. for a long time.

Figure 7A:
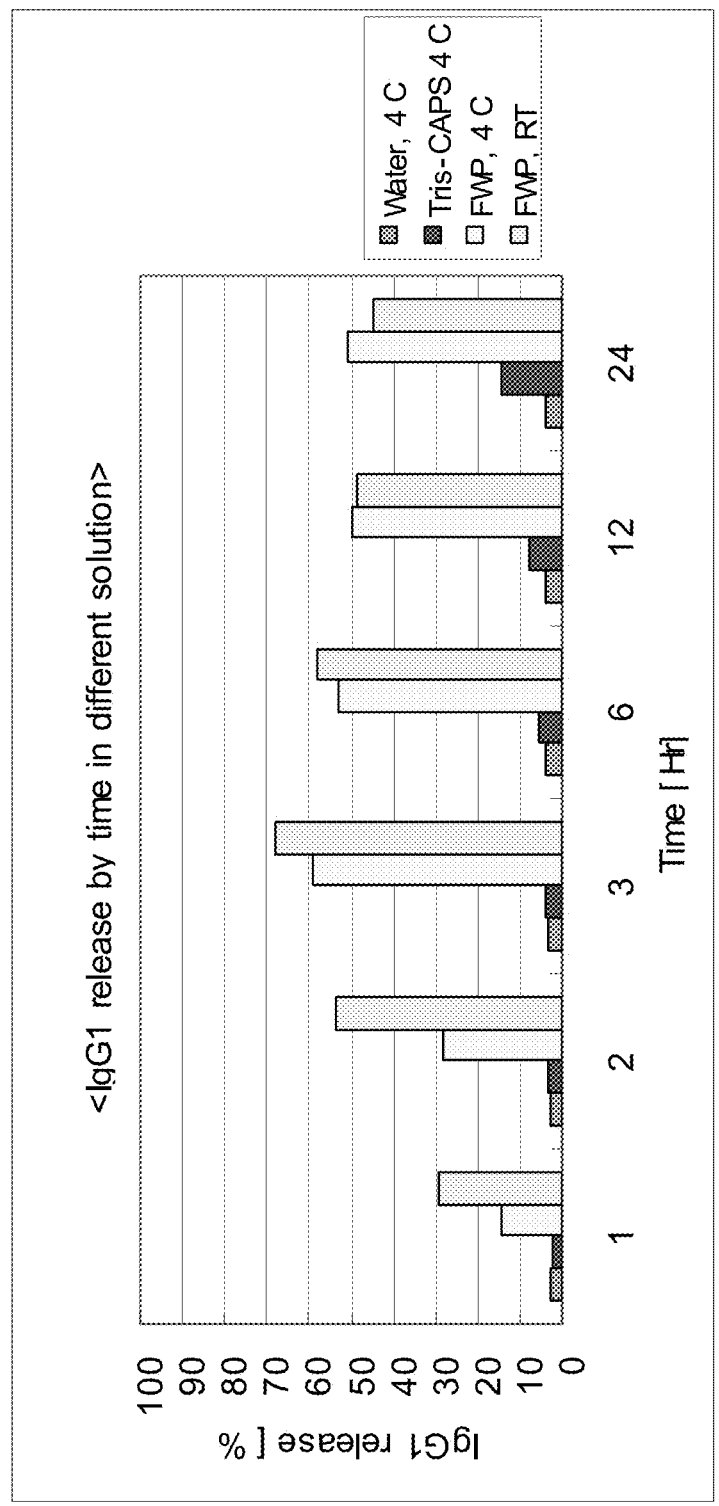
FIGS. 7A-B illustrate graphs comparing an IgG1 release profile by time up to 24 hr in water and Tris-CAPS buffer by diffusion and in FWP via hydrolysis.
Figure 7B:
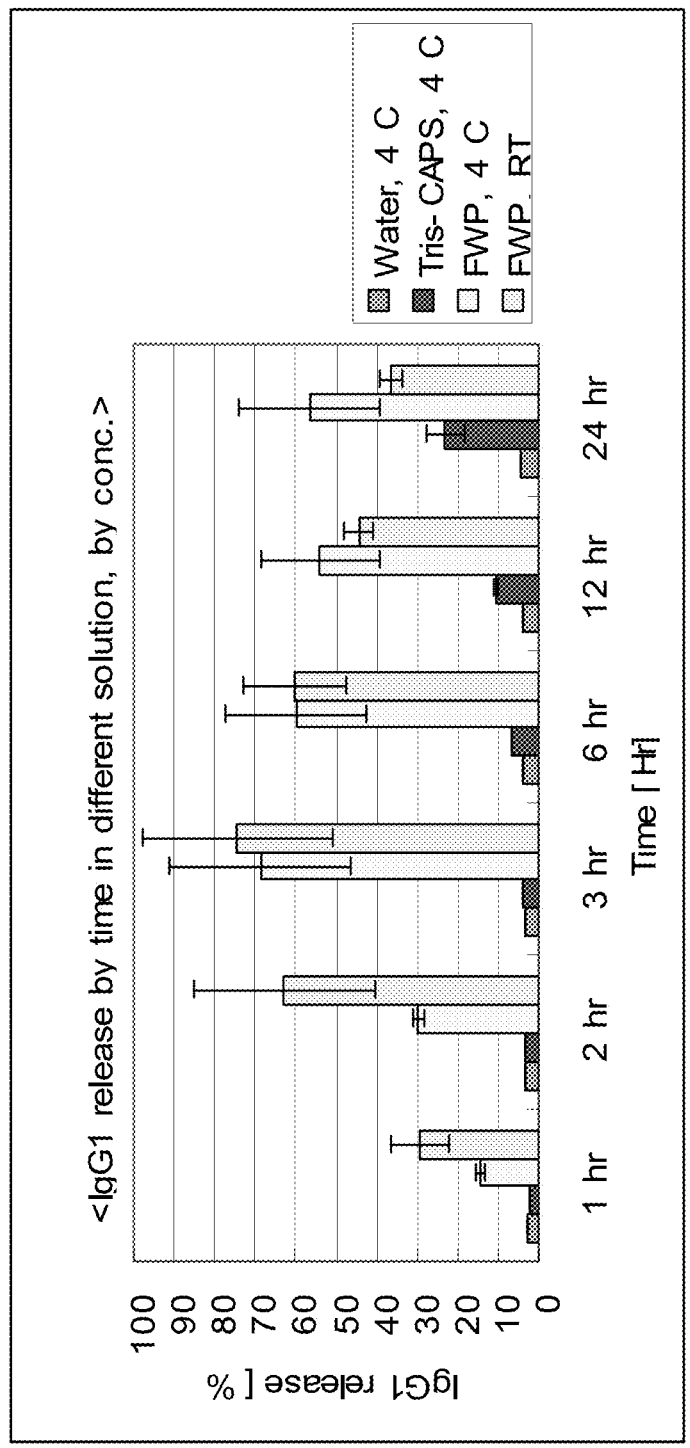

Referring to FIG. 7, protein was not diffused out much when incubated in water and Tris-CAPS, at most 23% after 24 hr incubation in Tris-CAPS buffer. In contrast, IgG1 was released up to 74% when hydrolyzed in FWP for 3 hours.

Novel technology to obtain rather large intact proteins from polyacrylamide gel using acid degradable acetal crosslinker was described. Activity of antibody IgG1 was preserved while running and hydrolyzing a gel in pH 3 solution, and the amount of released IgG1 from a gel was quantified by ELISA. This technology can be extended to 2-D gel eletrophoresis and applied to more complicated biological system in order to retrieve functionally active "intact" proteins.

EXAMPLE 2

Figure 8:
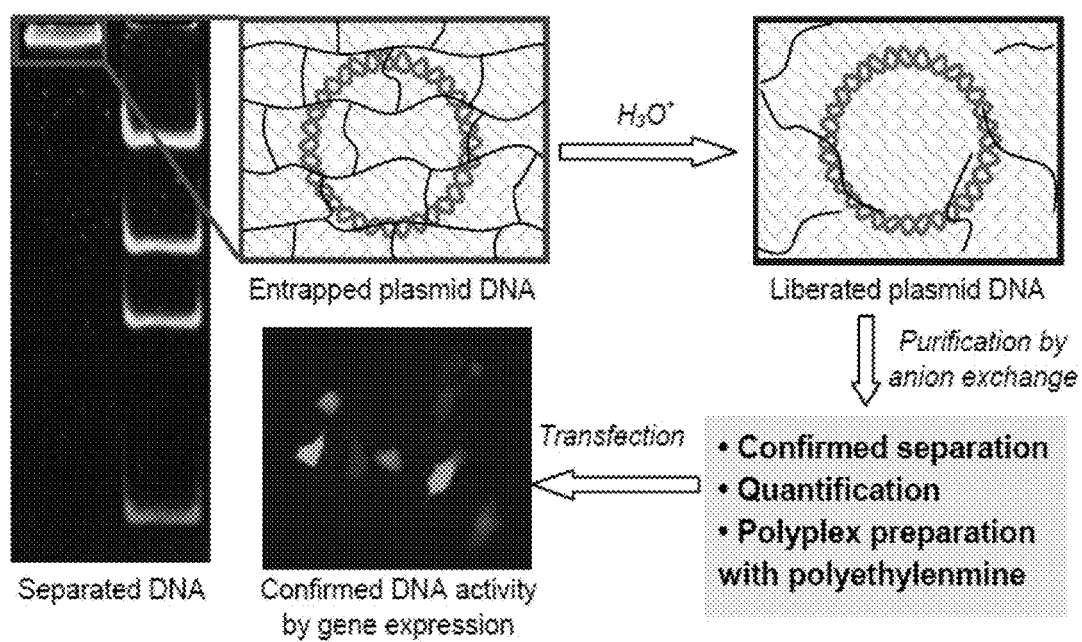
FIG. 8 is a schematic illustration of separation, isolation, and purification of nucleic acids using acid-degradable polyacryalmide gel electrophoresis, followed by confirmation of preserved structural and functional activities.

We examined whether the acid-degradable PAGE can be adapted for separation and recovery of nucleic acids, which require different separation, staining, and purification methods from proteins in FIG. 8. The results clearly demonstrated that almost 100% of nucleic acids were recovered when released from acid-degradable polyacrylamide gel, and 44-84% of further concentrated and purified nucleic acids were yielded. eGFP (enhanced green fluorescent protein)-encoding plasmid DNA recovered after acid-degradable polyacrylamide gel electrophoresis resulted in significantly enhanced cellular transfection. This new technique proposed a new approach to isolating and analyzing nucleic acids and other biomacromolecules.

Materials

The acid-degradable cross-linker, N,N'-(7,7-dimethyl-3,6,8,11-tetraoxamidecane-1,13-diyl)diacrylamide (ethoxy ketal bisacrylamide), was synthesized. Acrylamide, N,N'-methylenebisacrylamide, ammonium persulfate, TEMED, bromophenol blue, ethidium bromide, and 100~10,000 bp DNA ladder were purchased from Fisher Biotech (Fairlawn, N.J.) and 100~1,000 bp DNA ladder was purchased from Lonza (Rockland, Me.). Enhanced green fluorescent protein (eGFP)-encoding plasmid DNA was a generous gift from Dr. Pamela Davis (Department of Physiology and Biophysics, Case Western Reserve University, Cleveland, Ohio). Restriction enzymes Hind III and Pvu II (Promega, Madison, Wis.), and Spe I and Xmn I (New England Biolabs, Ipswich, Mass.) were used to digest the plasmid DNA.

Pre-swollen anion exchanger DE 52 (diethylaminoethyl cellulose) (Whatman, Florham Park, N.J.) and pre-packed Mini Macro-Prep High Q Cartridges (Bio-Rad, Hercules, Calif.) were used to purify plasmid DNA. The purified nucleic acids were further concentrated using a centrifugal filter (MWCO=10 kDa) (AMICON Ultra-15 from Millipore, Billerica, Mass.) and quantified by QuantiT™ PicoGreen dsDNA assay kit (Molecular Probes, Eugene, Oreg.). NIH 3T3 cells (ATCC, Rockville, Md.) were cultured in Dulbecco's modified Eagle's medium (DMEM) (MediaTech, Herndon, Va.) with 10% fetal bovine serum (FBS) (Hyclone, Logan, Utah). Purified DNA was complexed with branched polyethylenimine (25 kDa) (Sigma Aldrich, Milwaukee, Wis.) for transfecting the cells. All other chemicals and buffers were purchased from Fisher Scientific (Springfield, N.J.).

Acid-Degradable Polyacrylamide Gel Electrophoresis

Acid-degradable polyacrylamide gels were prepared by polymerizing acrylamide with acid-degradable ethoxy ketal bisacrylamide cross-linker, instead of cross-linking with conventionally used N,N'-methylene bisacrylamide. To ensure migration of the gigantic model nucleic acid (eGFP-encoding plasmid DNA, 5.0 kbps, ~1.6 million Da), 8% (w/w) gel with 5% (w/w) acid-degradable cross-linker was prepared. To assess separation, isolation, and purification of nucleic acids of various sizes, the eGFP plasmid DNA was fragmented by Spe I, Xmn I, Hin d III, and Pvu II restriction enzymes. A single site of the plasmid DNA was cut by each enzyme, yielding 423, 894, 1315, and 2349 bp fragments. For gel electrophoresis, 0.25~2 µg of whole plasmid DNA and its fragments were loaded in the well of a mini gel after being mixed with 30% (v/v) of glycerol and 0.01% (w/v) of bromophenol blue dye in TBE buffer (pH 8.2). The loaded nucleic acids were electrophoresed at 4° C. at 120 V for 120 min in TBE buffer before the electrophoresed gel was stained with 0.05% (w/v) of ethidium bromide (EtBr) solution. After being stained for 20 min, separated nucleic acids in the gel was visualized on a transilluminator and imaged using an Alphaimager (Alpha Innotech, San Leandro, Calif.).

Isolation and Purification of Nucleic Acids

Unstained bands of whole plasmid DNA and its fragments in the unstained gel, which were located by comparing the image of stained counterpart of the gel, were carefully excised using a sharp scalpel. The excised bands were hydrolyzed in 100 mM formic acid with 10% (v/v) of 2-propanol in water (FPW buffer, adjusted to pH 5) at 37° C. for 1~2 h with gentle shaking until the gel band was completely liquefied. It was confirmed that the activity of eGFP plasmid DNA was not affected after being incubated in 100 mM FPW buffer at pH 5 for 1-2 h, while 5 mM FPW at pH 3 significantly reduced its cell transfection capability (data not shown). The hydrolysis of the acid-degradable polyacrylamide gel bands were stopped by adding the equivalent volume of slightly basic TE buffer (50 mM Tris-HCl, 5 mM EDTA; pH 8) to the FPW hydrolysis buffer. The released nucleic acids were further purified from the hydrolyzed polyacrylamide matrix using a DE52 anion exchange resin. Pre-swollen DE resin in TE buffer [10% (v/v)] was added and incubated for 1 h at room temperature with agitation for resin suspension. After nucleic acid-adsorbing DE resins were pelleted by centrifugation at 4,500 rpm for 10 min at RT, the hydrolyzed polyacrylamide-containing supernatant was removed, and the remaining pellet was further washed twice with TE buffer. Nucleic acids bound to the DE resins were then eluted by flushing with 2 mL of TE buffer supplemented with 1.2 M NaCl and further concentrated using a centrifugal filter (MWCO=10 kDa). In order to ensure the removal of residual DE resins completely, recovered nucleic acids were further purified using ion exchange column. Five mL of recovered nucleic acids solution was loaded into a TE buffer-equilibrated Mini Macro-Prep High Q cartridge, made of polymer-based strong anion exchange resins providing quaternary amine functional groups. The column was washed with 15 mL of TE buffer and nucleic acids were eluted with 10 mL of TE buffer containing 0.2 M sodium chloride (pH 8), followed by eluting with 5 mL of TE buffer containing 1 M sodium chloride, at the flow rate of 0.5 mL/min using a syringe pump. Eluted nucleic acid solutions were concentrated using a centrifuge filter at 4,500 rpm for 15 min.

The amount of plasmid DNA and its fragments recovered after acid-degradable polyacrylamide gel electrophoresis and purification using the DE resins were quantified by double stranded DNA assay kit. Recovery of plasmid DNA and its fragments was also qualitatively confirmed by a second conventional (non-degradable) polyacrylamide gel electrophoresis. Purified nucleic acids were loaded in a 8% (w/w) polyacrylamide gel cross-linked by 2.67% (w/w) N,N'-methylene bisacrylamide for the second gel electrophoresis, which resulted in the similar molar cross-linking ratio to 8% acid-degradable polyacrylamide gel cross-linked by 5% acid-degradable cross-linker, followed by EtBr staining under the same conditions employed for acid-degradable polyacrylamide gel. Reappearance of the bands in the identical locations as shown in a degradable polyacrylamide gel indicates that the electrophoretic properties such as molecular weights (MWs) and net charges of the nucleic acids were preserved through gel electrophoretic separation, isolation from the gel, and purification from hydrolyzed polyacrylamide.

Cell Transfection by Plasmid DNA Recovered from Acid-Degradable Polyacrylamide Gel Functional intactness of the plasmid DNA recovered from a degradable polyacrylamide gel was confirmed by eGFP expression in the cells transfected by plasmid DNA/polyethylenimine (PEI) polyplexes. NIH 3T3 cells were inoculated at a density of $2 \times 10^4$ cells/well in a 24-well plate, 24 h prior to transfection. Plasmid DNA/PEI polyplexes were prepared by mixing 1 μg of purified eGFP plasmid DNA in 100 μL of DI water with 100 μL of 2.6 μg/mL branched PEI (25 kDa) in PBS, resulting in the final volume of 200 μL. Prepared plasmid DNA/PEI polyplexes were incubated for 15 min at room temperature and added to cell-containing wells with an additional 400 μL of DMEM at 37° C. After 4 h of incubation, the medium was replaced with 1 mL of fresh DMEM supplemented with 10% fetal bovine serum (FBS) and the cells were further incubated for another 24 h. eGFP expression was observed under Olympus IX-71 inverted fluorescence microscope. Transfection rate and mean gene expression intensity (mean fluorescence intensity, MFI) were quantified by flow cytometry using a Guava EasyCyte cytometer (Guava Technologies, Hayward, Calif.).

Results

Acid-degradable polyacrylamide gels were prepared by polymerizing acrylamide with acid-degradable ethoxy ketal bisacrylamide cross-linker, N,N'-(7,7-dimethyl-3,6,8,11-tetraoxamidecane-1,13-diyl)diacrylamide, instead of crosslinking with conventionally used N,N'-methylene bisacrylamide. Native enhanced green fluorescent protein (eGFP)-encoding plasmid DNA (4981 bps, ~1.6 million Da) produced in *E. coli* was purified using a Qiagen plasmid DNA purification kit and stored in nuclease-free DI water at −80° C., followed by being thawed immediately before use. The plasmid DNA and its fragments (423, 894, 1315, and 2349 bps), sliced by SpeI, XmnI, Hind III, and PvuII restriction enzymes, were loaded to a 8% w/w mini gel with 5% w/w acid-degradable cross-linker (3 μg per well in 20 μl of loading buffer) and electrophoresed at 4° C. at 120 V for 120 min in TBE buffer. The electrophoresed gel was then cut in half to obtain two identical gel pieces. Separated nucleic acid bands in the gel was visualized on a transilluminator and imaged using an Alphaimager (Alpha Innotech, San Leandro, Calif., USA) after a half of the electrophoresed gel was stained with 0.05% w/v of ethidium bromide (EtBr) solution. For liberating entrapped DNA fragments in the gel, each gel band in the unstained other half gel, located by comparing the image of the stained counterpart of the gel, was carefully excised and incubated in a mildly acidic buffer solution (pH 5.0), instead of crushing identified gel bands, which gives low recovery efficiency even after a long incubation time. It should be noted that the hydrolysis conditions had to be optimized for rapid hydrolysis of acid-degradable polyacrylamide gel while preserving structural and functional intactness of nucleic acids. It was identified that 100 mM formic acid with 10% v/v of 2-propanol in water (FPW hydrolysis solution; adjusted to pH 5.0 by adding NaOH) efficiently cleaved the acid-cleavable cross-linkers for 1-2 h at 37° C. without any obvious changes in cellular transfection activity of the plasmid DNA (data not shown). The hydrolysis of the acid-degradable polyacrylamide gel bands were stopped by adding the equivalent volume of slightly basic TE buffer (50 mM Tris-HCl, 5 mM EDTA; pH 8) to the FPW hydrolysis solution. The released nucleic acids were further purified from the hydrolyzed polyacrylamide matrix using a pre-swollen diethylaminoethyl cellulose (DE)52 anion exchange resin (Whatman, Florham Park, N.J., USA). After removal of the hydrolyzed polyacrylamide-containing supernatant by centrifugation, nucleic acids bound to the DE resins were then eluted by flushing with TE buffer supplemented with 1.2M NaCl and further concentrated using a centrifugal filter (molecular weight cut-off (MWCO) =10 kDa, AMICON Ultra-15 from Millipore, Billerica, Mass., USA). In order to ensure the removal of residual DE resins completely, recovered nucleic acids were further purified using an ion exchange column (IEC) (prepacked Mini Macro-Prep High Q cartridge, Bio-Rad, Hercules, Calif., USA), and eluted nucleic acid solutions were concentrated using a centrifuge filter (MWCO=10 kDa).

Figure 9:
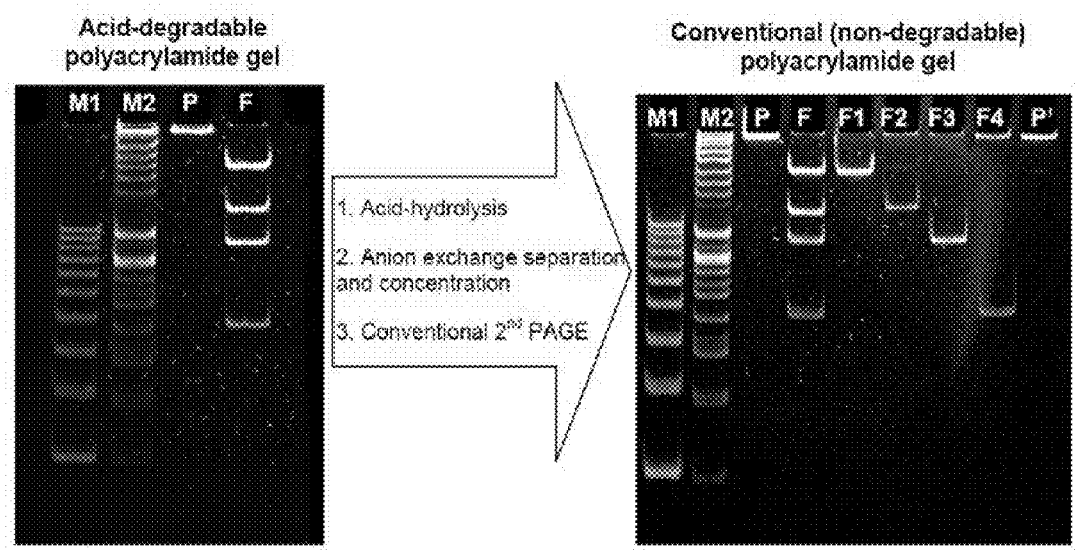
FIG. 9 illustrates separation and recovery of structurally intact plasmid DNA and its fragments using acid-degradable polyacrylamide gel electrophoresis. Left: eGFP-encoding plasmid DNA and its digested fragments electrophoresed in a degradable polyacryalmide with DNA ladders (0.1~1 and 0.1~10 kbps ladder), stained in EtBr solution, and then imaged under short wavelength (302 nm) UV (M1: 0.1~1 kbp ladder, M2: 0.1~10 kbp ladder, P: plasmid DNA, F: digested fragments). Right: Second gel electrophoresis in a conventional polyacrylamide gel loaded with nucleic acids recovered from individual bands of first acid-degradable polyacrylamide gel through gel hydrolysis, concentration, and purification.

The efficiency of nucleic acid recovery from acid-degradable polyacrylamide gel after electrophoresis was quantified by comparing the amounts of the plasmid DNA and its fragments initially loaded in the gel. The recovery of eGFP-encoding plasmid DNA (4981 bps, ~1.6 MDa) was particularly focused because of its notable size, which makes isolating it from conventional polyacrylamide gel extremely difficult. To avoid counting in unhybridized and fully hydrolyzed nucleic acids, a dsDNA quantification kit was used rather than using UV absorbance. Almost complete recovery of the whole plasmid and its fragments were obtained after first purification using DE resin, except for the size of 894 bps (Table 1). To reduce the volume and obtain completely pure nucleic acids from any residual DE resin and traceable amounts of hydrolyzed polyacrylamide, recovered nucleic acids were further concentrated and purified using a centrifugal filter and a pre-packed IEC, which further lowered recovery efficiency in the range of 44-84%, as shown in Table 1. It should be noted that, for comparison, only approximately 2% of plasmid DNA was recovered from a conventionally used non-degradable polyacrylamide gel using the same electrophoresis, incubation in FPW solution, purification, and concentration methods.

sizes initially mixed together (Lane F) were recovered separately after individual bands were cut and hydrolyzed, followed by nucleic acid isolation and purification (Lanes F1-F4 in FIG. 9).

TABLE 1

Recovery of plasmid DNA and its frgments via acid-degradable PAGE, and non-degradable agarose and conventional PAGE

|  |  | Plasmid DNA | F1 | F2 | F3 | F4 |
|---|---|---|---|---|---|---|
| Size of nucleic acid (bps) |  | 4981 | 2349 | 1315 | 894 | 423 |
| Recovery via degradable PAGE | After resin purification (%) | 100 | 110 | 101 | 83 | 101 |
|  | After resin purification and centrifugal concentration (%) | 65 | 105 | 92 | 70 | 66 |
|  | After resin purification, centrifugal concentration, and IEC Chromatography (%) | 45 | 77 | 84 | 44 | 55 |
| Recovery from non-degradable gel using QIAEX II kit | From an agarose gel (%) | ~1 | 42 | 82 | 85 | 98 |
|  | From a conventional polyacrylamide gel (%) | ~1 | <1 | ~1 | ~1 | 3 |

The nucleic acid recovery efficiency after acid-degradable PAGE was also compared with one using a commercial kit from agarose and conventional polyacrylamide gels. In total, 3 μg of plasmid DNA and its fragments were loaded on the 1% agarose gel containing 1 μg/mL of EtBr. After electrophoresis in TBE buffer at 110 V for 60 min, separated nucleic acid bands were then visualized under a UV transilluminator and each gel band was excised. The nucleic acids were isolated from the excised agarose gel bands using a QIAEX II gel extraction kit (Qiagen, Valencia, Calif., USA), as instructed by the manufacturer's protocols. Eluted DNA was quantified using a dsDNA quantification kit. A conventional 8% w/w polyacrylamide gel with 2.2% w/w N,N'-methylene bisacrylamide cross-linker was also prepared and run under the same conditions used for acid-degradable PAGE. The separated DNA and its fragments were isolated using a QIAEX II gel extraction kit. As shown in Table 1, fair amounts of DNA fragments were recovered from an agarose gel using a QIAEX II gel extraction kit (Qiagen). The recovery of DNA and its fragments from an agarose gel was highly size-dependent (i.e., higher recovery of smaller DNA fragments). However, almost no plasmid DNA was recovered from an agarose gel using a QIAEX II kit. From a conventional polyacrylamide gel, plasmid DNA and its fragments were barely recovered using the QIAEX II kit. This comparison result clearly demonstrates the superior nucleic acid recovery via acid-degradable PAGE to conventional and commercially available methods.

Figure 10:
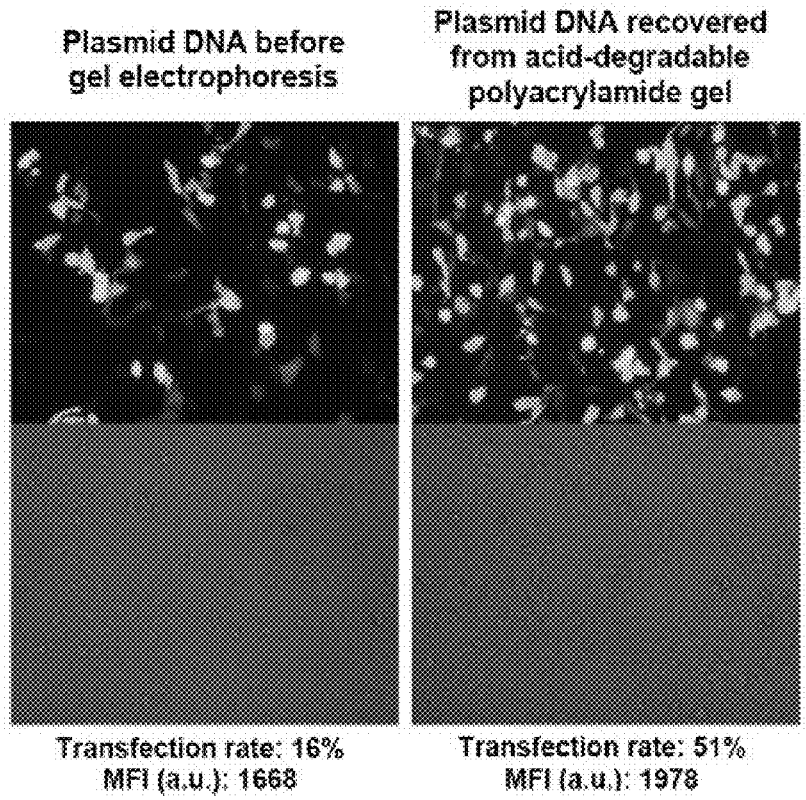
FIG. 10 illustrates fluorescent (Top) and phase contrast (Bottom) micrographs of eGFP-expressing NIH 3T3 cells transfected by the polyplexes prepared with un-electrophoresed plasmid DNA (Left) and the polyplexes prepared with the plasmid DNA recovered from acid-degradable polyacrylamide gel (Right). Transfection rate and mean fluorescence intensity (MFI) were measured by flow cytometry.

Recovery of nucleic acids from acid-degradable polyacrylamide gels after purification was also confirmed by the second gel electrophoresis using a conventionally used (nondegradable) polyacrylamide gel (FIG. 9). The same molar cross-linking ratios were used to prepare both acid-degradable and conventional polyacrylamide gels. The whole plasmid DNA (Lane P') and its fragments (Lanes F1-F4) that were recovered from acid-degradable polyacrylamide gel showed no differentiable electrophoretic properties (e.g., molecular weights, hydrodynamic size, and net charges), compared with the starting plasmid DNA (P) and fragments (F) (FIG. 9). It was clearly demonstrated that DNA fragments of different Preserved electrophoretic properties do not guarantee functional intactness of nucleic acid recovered from a degradable polyacrylamide gel. To simulate a validation of the biological function of a gene isolated from a biological sample that is separated by acid-degradable gel electrophoresis and recovered by gel hydrolysis and purification, the eGFP-encoding plasmid DNA separated and purified as described earlier was used to transfect NIH 3T3 murine fibroblast cells. Since naked plasmid DNA has highly limited cellular internalization and transfection capabilities, recovered plasmid DNA was further polyplexed with a popularly used polymeric trasnfection agent, branched polyethylenimine (PEI, 25 kDa). For comparison, the same amount of the plasmid DNA that had not been electrophoresed was used to prepare polyplexes. The cells were then incubated with the polyplexes and their eGFP expression was confirmed qualitatively by fluorescence microscopy as well as quantitatively by flow cytometry. As shown in FIG. 10, the recovered plasmid DNA was able to transfect the cells with significantly higher efficiency (higher than threefold) than the starting unelectrophoresed DNA. Relative gene expression level, quantified as mean fluorescence intensity (MFI) measured by flow cytometry, was also higher when the plasmid DNA recovered from an acid-degradable polyacrylamide gel was used to transfect the cells, in comparison with un-electrophoresed plasmid DNA. In order to find out what process improved the transfection capability of the electrophoretically separated and purified plasmid DNA, un-electrophoresed plasmid DNA was incubated in the FPW hydrolysis solution, purified by anion exchange resin, concentrated by centrifugal filtration, and further purified ion exchange column (e.g., only acid-degradable PAGE was skipped), as described earlier. The resulting plasmid DNA did not show any differentiable transfection efficiency, compared with starting plasmid DNA (data not shown). In addition, both un-electrophoresed plasmid DNA and the plasmid DNA recovered from an acid-degradable polyacrylamide gel showed no noticeably different PCR efficiency (Table 2). Quantitative PCR (qPCR) was performed using an ABI PRISM 7000 Sequence Detector (Applied Biosystems, Foster City, Calif., USA). SYBR Green PCR Master mix (Applied Biosystems) was used to detect dsDNA after each amplification cycle. The reaction was carried out in a volume of 5 µL containing 1.5 µL of DNA, 0.5 µL of each primer, and 2.5 µL of SYBR Green master mix. The amount of plasmid DNA recovered from a degradable polyacrylamide gel to perform qPCR ranged from 1 to 0.01 pg. The same amount of plasmid DNA, which had not been electrophoresed, was also subjected to qPCR for comparison. Each PCR comprised 40 cycles with denaturing at 95° C. for 15 s, annealing at 60° C. for 20 s, and extension at 72° C. for 40 s after an initial denaturation step at 95° C. for 10 min, followed by incubation at 95° C. for 15 s, 60° C. for 15 s, and 95° C. for 15 s for the dissociation curve. As indicated in Table 2, the threshold cycle number of recovered and purified plasmid DNA obtained from PCR was almost the same as the plasmid DNA, which had not been electrophoresed, showing that PCR efficiency of plasmid DNA was not changed during acid-hydrolysis of a degradable gel and DNA recovery process. These results indicate that acid-degradable PAGE enhanced biological activity (transfection) of the plasmid DNA, possibly by removing biologically inefficient forms of plasmid DNA and/or impurities that are quantified (e.g., PCR) but interfere with biological activity. The results demonstrated that the biological activity of the plasmid DNA that was electrophoretically separated in an acid-degradable polyacrylamide gel and further recovered by gel hydrolysis and anion exchange purification was significantly improved, which implies that studying the activity of an unknown nucleic acid recovered from a biological sample via acid-degradable PAGE is highly feasible.

TABLE 2

PCR efficiency of un-electrophoresed plasmid DNA and the plasmid DNA recovered after acid-degradable PAGE

| | Threshold cycle number from PCR | |
|---|---|---|
| DNA Amount (pg) | Un-electrophoresed | Recovered from an acid-degradable polyacrylamide gel |
| 0.01 | 21 | 21.6 |
| 0.1 | 18.3 | 18.7 |
| 1 | 15.8 | 15.9 |

Not only DNA but also RNA can be easily separated by the same methods. Silencers GFP siRNA (Ambion, Austin, Tex., USA) was electrophoresed at 100 V for 60 min followed by band excision and acid-hydrolysis under the same conditions used for DNA isolation. An AMICON Ultra-4 centrifugal filter (MWCO=3 kDa) (Millipore) was used to concentrate siRNA. Table 3 demonstrates that approximately a third of siRNA was recovered after degradable PAGE, hydrolysis in the pH 5.0 FPW solution, and multi-step purification/concentration processes. Gene silencing efficiency of the siRNA isolated from acid-degradable polyacrylamide gel was also quantified by comparing the gene silencing efficiency of un-electrophoresed GFP siRNA. Briefly, eGFP-expressing NIH 3T3 cells were inoculated at a density of $2\times10^4$ cells/well in a 24-well plate and they were transfected by the siRNA/PEI polyplexes as described in FIG. 10 (i.e., 1 µg of siRNA and 2.6 µg of branched PEI). eGFP silencing effect was quantified by reduced MFI measured by flow cytometry, after 64 h of incubation. The gene silencing efficiencies of the unelectrophoresed siRNA and the recovered siRNA after acid-degradable gel electrophoresis were determined to be 55 and 49%, respectively (Gene silencing by un-electrophoresed siRNA with a scrambled sequence (negative control siRNA): 11%). The recovered siRNA showed almost 90% preserved silencing capability, compared with un-electrophoresed siRNA.

This result implies that RNA, which is chemically labile more than DNA, can be separated and recovered via acid-degradable PAGE. In conclusion, a new paradigm of separating nucleic acids of various sizes and efficiently recovering them with preserved structural and functional properties by utilizing a novel polyacrylamide gel degradable under a mildly acidic condition was demonstrated. This highly efficient and convenient technique can be further perfected in combination with improving nucleic acid concentration and purification from hydrolyzed polyacrylamide.

TABLE 3

Recovery of siRNA (23 bps) via acid-degradable PAGE

| | |
|---|---|
| After resin purification (%) | 98 |
| After resin purification and centrifugal concentration (%) | 42 |
| After resin purification, centrifugal concentration, and IEC chromatography (%) | 30 |
| Preserved gene silencing efficiency of siRNA recovered from acid-degradable polyacrylamide gel after resin purification, centrifugal concentration, and IEC chromatography (% | 89 |

EXAMPLE 3

Figure 11:
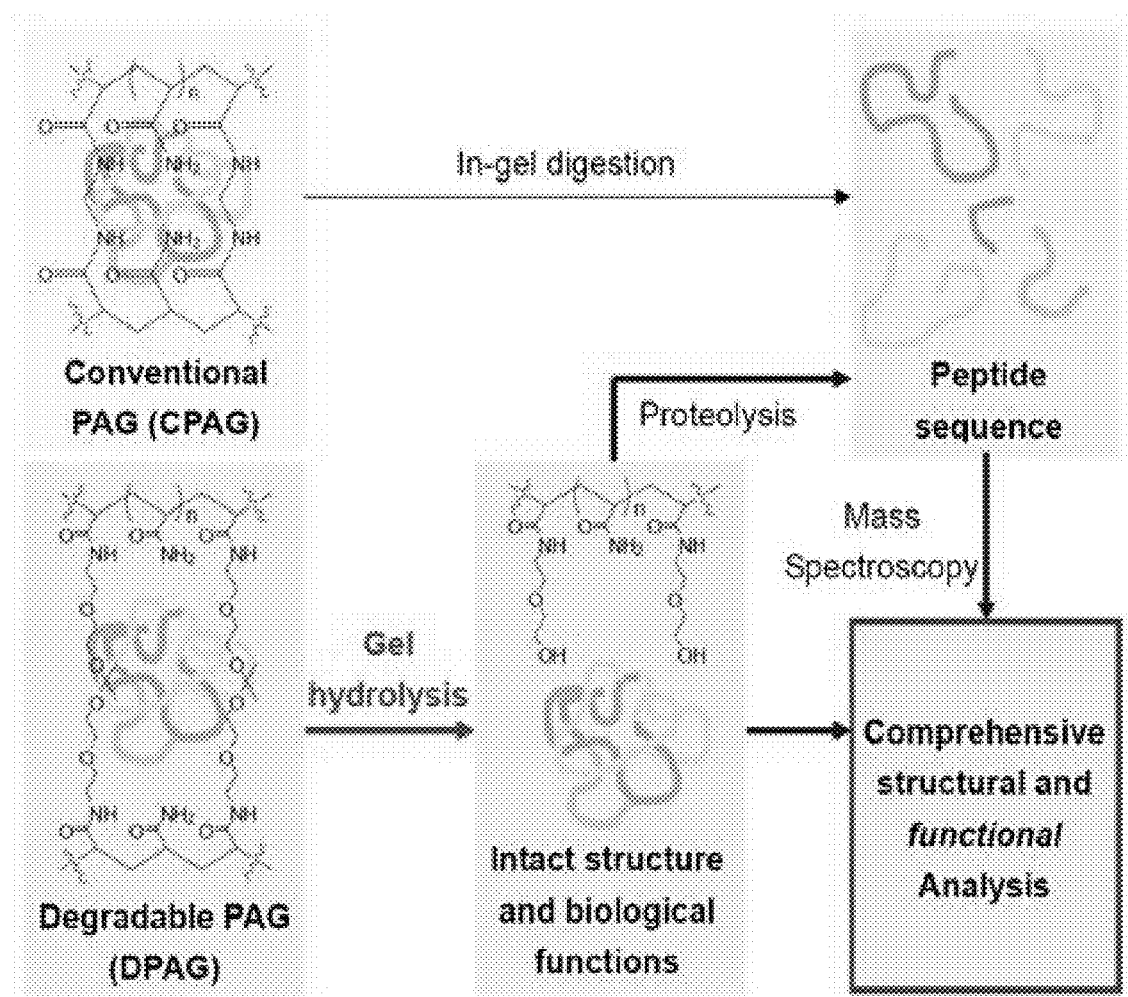
FIG. 11 illustrates comparison of different routes of analysis of a protein separated by polyacrylamide gel electrophoresis (PAGE) using conventional polyacrylamide gel (CPAG) and degradable polyacrylamide gel (DPAG). The schematic compares structural and functional analysis of a protein isolated from a DPAG (bold arrows) and limited peptide sequence-based structural analysis of fragmented peptides isolated from a CPAG (thin arrows).
Figure 12:
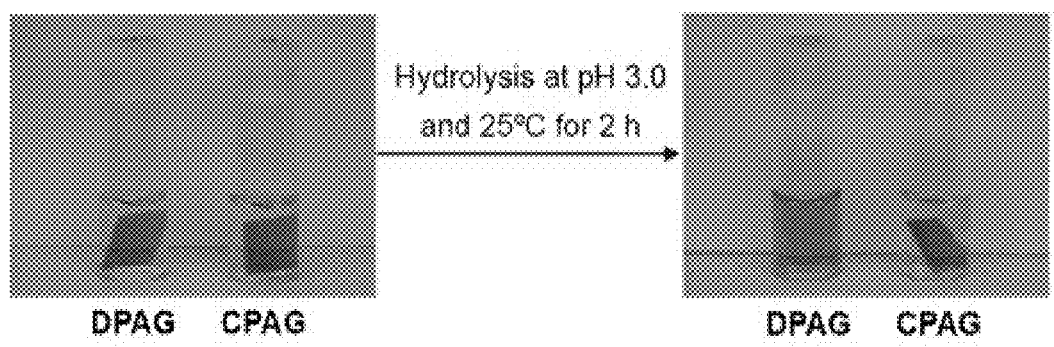
FIG. 12 illustrates A DPAG and a CPAG piece before and after incubation in FWP hydrolysis solution for 2 h at R.T. The gel bands were silver stained for visualization.

A novel method of isolating intact proteins was developed by hydrolyzing the polyacrylamide gel under a mildly acidic condition, rather than fragmenting the proteins. Both structural and functional analysis of a protein is feasible using this new approach (bold arrows in FIG. 11), while conventional polyacrylamide gel electrophoresis offers limited peptide sequence-based structural analysis of fragmented peptides (thin arrows in FIG. 11). Acid degradable polyacrylamide gel (DPAG) was prepared using aciddegradable cross-linker, N,N'-(7,7-dimethyl-3,6,8,11-tetraoxamidecane-1,13-diyl) diacrylamide, instead of conventionally used N,N''-methylenebisacrylamide. Monoclonal antibodies (IgG1 type, 150 kDa) that specifically bind to H-2K (MHC I)/SIINFEKL (ovalbuminderived peptide), was electrophoresed in the newly formulated degradable gel at 10% total weight with 5% cross-linking ratio (i.e., optimized DPAG formulation for mouse IgG1 separation), using Tris-3-(cyclohexylamino)-1-propanesulfonic acid (CAPS) solution (pH 9.6) as a running buffer without any reducing agents and sodium dodecylsulfate (SDS) (i.e., native gel electrophoresis). The gel bands were visualized by silver staining without fixation by acetic acid or glutaraldehyde. In order to quantify protein release efficiency from a degradable gel band after hydrolysis, mouse IgG1 was electrophoresed in a pair of DPAG as described earlier. After electrophoretic separation, one DPAG gel was silver stained and the other remained unstained since it was previously reported that repeated gel electrophoresis of silver-stained proteins was irreproducible due to structural alteration and/or immobilization of proteins, possibly resulted from cross-linked lysine residues and precipitated/fixed proteins in the gel. The unstained DPAG bands corresponding to the IgG1 band in the stained gel, which was observed in the top of the gel, were excised. Each excised band was then incubated in the hydrolysis solution, 5 mM formic acid and 10% (v/v) of 2-propanol (FWP, pH 3.0) in water, for 2 h at room temperature with gentle shaking. As shown in FIG. 12, degradable polyacrylamide gel (DPAG) cross-linked by 5% acid-cleavable cross-linkers with 10% monomer concentration, was shown to be completely liquefied after being incubated in pH 3.0 FWP hydrolysis solution, at room temperature for 2 h, while conventional polyacrylamide gel (CPAG), cross-linked by methylene bis-acrylamide, was stable under the same conditions even for months.

Figure 13:
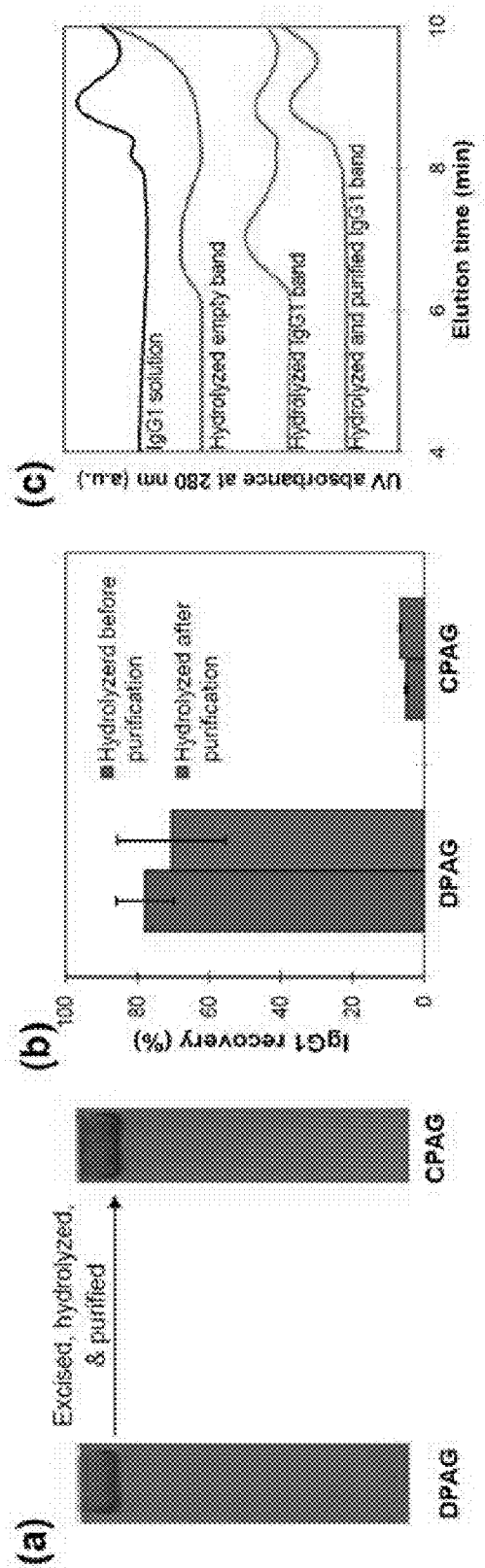
FIGS. 13A-C illustrate purified proteins were confirmed by (a) a second gel electrophoresis using CPAG followed by silver staining, (b) ELISA for quantification of recovered amount of IgG1 from DPAG and CPAG electrophoresis before and after purification from hydrolyzed polyacrylamide using selective precipitations, and (c) GPC analysis of IgG1 alone (black), hydrolyzed blank DPAG band (blue), hydrolyzed DPAG band of IgG1 before purification (green), and hydrolyzed DPAG band of IgG1 after purification by precipitation (red). Data were presented as mean±s.d. (n=3, $\alpha$=0.05, and P=$2.71 \times 10^{-6}$ for recovered IgG1 from DPAG and CPAG after hydrolysis before purification; n=3, $\alpha$=0.05, and P=$2.74 \times 10^{-5}$ after purification; both by one-tailed ANOVA).

When a gel band was completely liquefied in FWP solution, the released protein was further purified from hydrolyzed polymer matrix by gradually adding acetonitrile up to 40~50% (v/v) of total volume followed by vigorous mixing. Precipitation is simple, applicable to the separation of a wide range of proteins, and easily scaled-up. Isolation of intact proteins was qualitatively and quantitatively confirmed by a second electrophoresis, enzyme-linked Immunosorbent assay (ELISA), and gel permeation chromatography (GPC) (FIG. 13). The purified proteins were re-loaded in a CPAG for second electrophoresis, followed by silver staining, both under the same conditions employed for degradable polyacrylamide gel electrophoresis (DPAGE) (FIG. 13A). A band in the identical location as that in a DPAG proves that the starting and purified proteins had the same electrophoretic properties (e.g., molecular weights and net charges). The overall efficiency of IgG1 isolation from DPAG and CPAG followed by selective precipitation were 71 and 7%, respectively, by ELISA (FIG. 13B). Approximately 60% of the IgG1 also was recovered from hydrolyzed polyacrylamide gel after purification using ion exchange chromatography (data not shown). Purification of proteins from hydrolyzed polyacrylamide was confirmed by GPC under UV detection at 280 nm. After purification, only IgG1 elution peak was shown, while two peaks representing IgG1 and hydrolyzed polyacrylamide were observed after hydrolysis without further purification (FIG. 13C).

Figure 14:
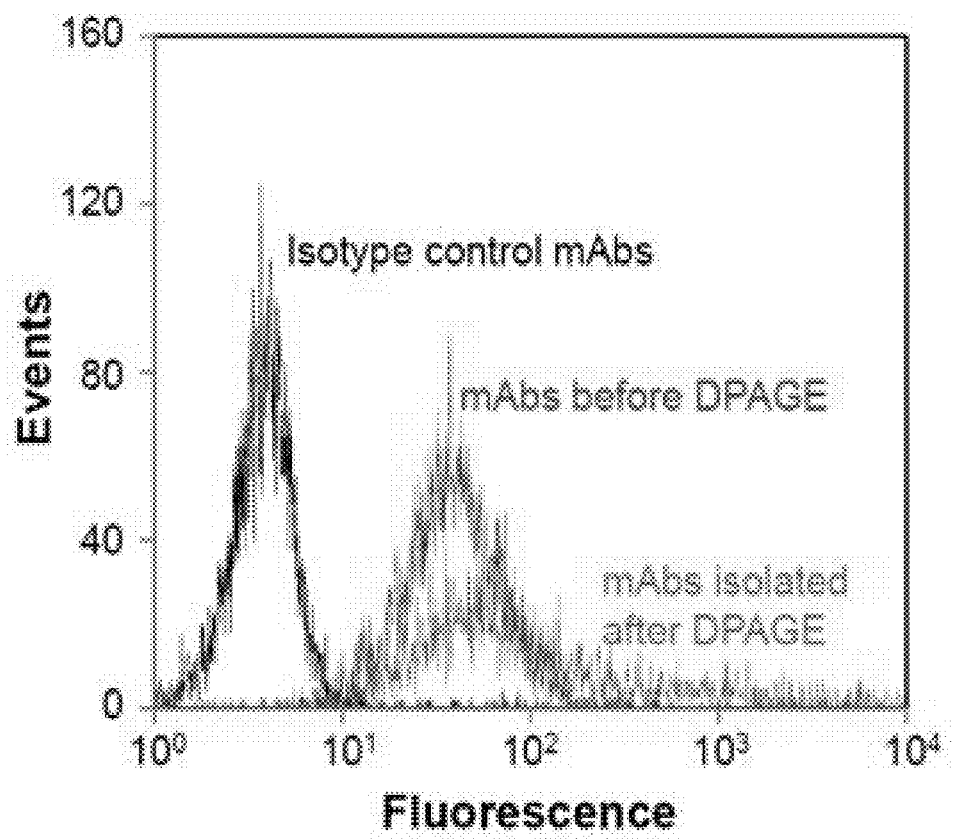
FIG. 14 illustrates preserved biological activity of the isolated IgG1 after degradable polyacrylamide gel electrophoresis (DPAGE), confirmed by specific antigen binding. Specific binding efficiency of isotype control, IgG1 before DPAGE, and IgG1 isolated after DPAGE to SIINFEKL/H2-K complexes on EL-4 cells was compared by flow cytometry.

EL4 mouse lymphoma cells presenting SIINFEKL peptides on H2-Kb MHC class I molecules (the antigen of the antibodies) were incubated with isolated IgG1 in order to confirm the preserved specific binding capability of the isolated antibodies to target antigens. Specific binding of the antibodies were further fluorescently marked by PEconjugated anti-mouse IgG1 antibody as a secondary antibody and quantified by flow cytometry. As control, PE-conjugated isotype mouse IgG1 antibodies were also incubated with the EL-4 cells presenting SIINFEKL/H2-Kb complexes. FIG. 14 demonstrates that the antibodies isolated after DPAGE preserved highly specific binding capability to target antigens.

Figure 15:
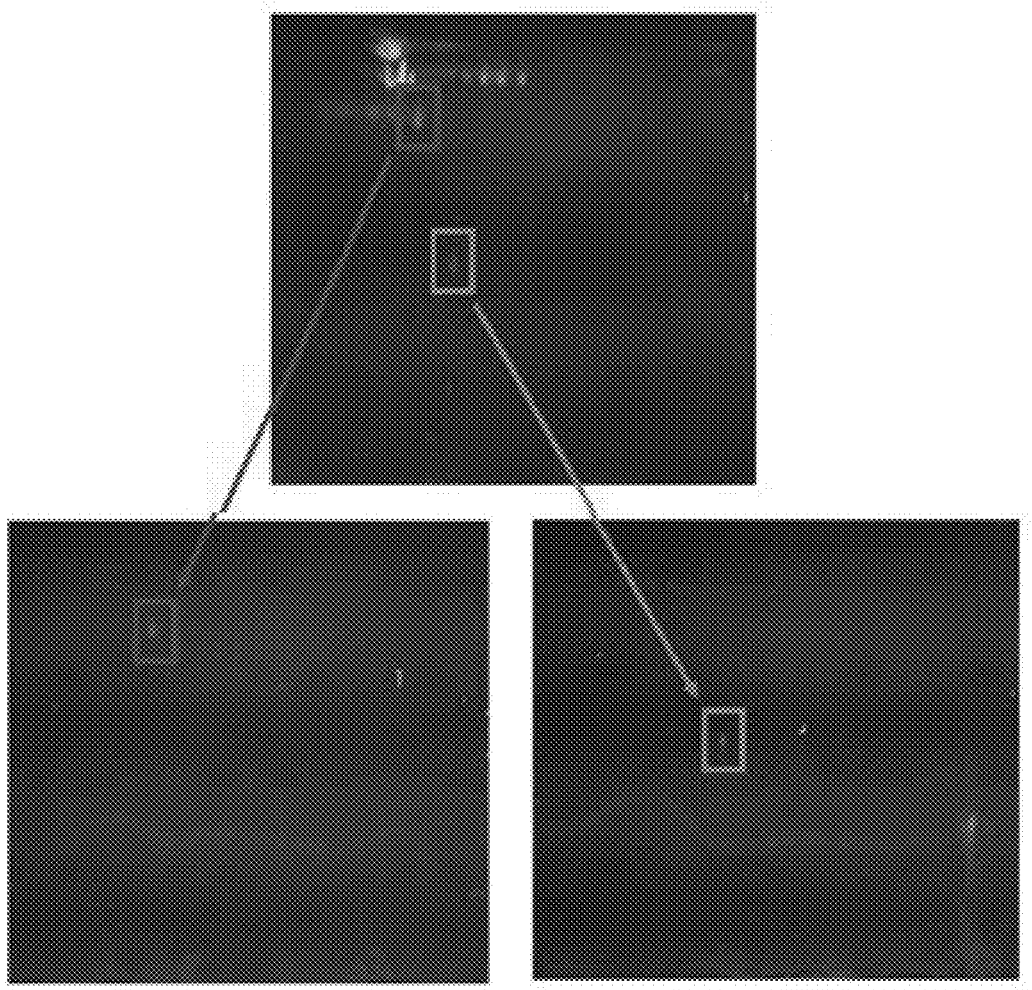
FIG. 15 illustrates osolation of protein spots from 2-D SDSDPAGE into separated 2-D gels. Identified spots were excised and hydrolyzed, and the isolated proteins were loaded into individual second 2-D gels.

The feasibility of simultaneously isolating a multiple number of proteins at their molecular weights as well as pI values using denatured 2-D SDS-DPAGE was explored using a model protein mixture containing BSA, IgG1, HRP, β-galactosidase, and alkaline phosphatase. After being stained by Deep Purple, which reversibly binds to lysine, arginine, and histidine residues in proteins and works in a basic solution (pH 10.5), the 2-D DPAG was visualized using a 365 nm UV transilluminator. Two bright spots were excised and hydrolyzed, and isolation of structurally intact proteins was confirmed by second 2-D SDS-CPAGE (FIG. 15). Reappearance of the bright spots at the same locations implies isolation of intact proteins from a 2-D SDS-DPAGE. Typically, 2-D PAGE is performed under denaturing conditions (i.e., urea, DTT, and detergents in rehydration buffer for isoelectrofocusing and electrophoresis running buffer). If proteins are isoelectrofocused and eletrophoresed under the conditions that keeps native states of proteins, it is probable to separate a number of structurally and functionally intact proteins by native 2D DPAGE.

A novel technique for isolating intact proteins after polyacrylamide gel electrophoresis was achieved. Instead of fragmenting proteins or physically dismantling gels, which results in loss of protein structure and function or yields, large intact proteins were isolated by hydrolyzing acid-degradable polyacrylamide gel. After purification from hydrolyzed polyacrylamide by precipitation, approximately 70% of native IgG1 (150 kDa) was obtained and the biological activity of the purified IgG1 was shown to preserve its specific antigen binding capability, while only a traceable amount of the antibodies were isolated from a conventionally used nondegradable polyacrylamide gel. The results clearly demonstrate that hydrolyzing polyacrylamide substantially enhanced (or simply enabled) intact protein recovery, and particularly, unlike the electroeluting method, this technique is applicable at any scales of PAGE and does not require additional equipment. Therefore, sufficient amounts of intact proteins for crystallography, atomic force microscopy, electron microscopy, nuclear magnetic resonance analysis, and functional assays of a protein isolated from PAGE can be achieved. Since there are no limits in protein size for efficient release from the degradable gel, gigantic proteins and protein/protein complexes can easily be separated and isolated possibly in their native forms. Also, applications of degradable gel electrophoresis could be expanded to simultaneously separate and isolate other biological and non-biological macromolecules and complexes such as nucleic acids, viruses, and synthetic nanomaterials in their intact forms.

From the above description of the invention, those skilled in the art will perceive improvements, changes and modifications. For example, it should be appreciated that the degradable polyacrylamide gel of the present invention can also be used in place of gels traditionally used in Western blotting. Such improvements, changes and modifications within the skill of the art are intended to be covered by the appended claims.

Having described the invention, the following is claimed:

1. A method of determining the functional activity of at least one polynucleotide, polynucleotide complex, virus, polynucleotide-protein complex, protein or protein complex in a cell, the method comprising the steps of:

obtaining a biological sample comprising at least one polynucleotide, polynucleotide complex, virus, polynucleotide-protein complex, protein or protein complex;

providing an electrophoresis device that includes a degradable polyacrylamide gel, the degradable polyacrylamide gel comprising a polyacrylamide that is cross-linked with at least one degradable cross-linker, the degradable cross-linker including a ketal or acetal group having the formula (I):

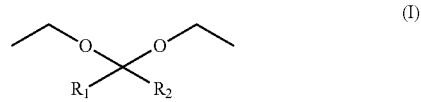

wherein $R_1$ and $R_2$ are the same or different and are hydrogen, an alkyl, or a substituted alkyl;

loading the biological sample into the degradable polyacrylamide gel; and performing electrophoresis on the degradable polyacrylamide gel to separate the at least one polynucleotide, polynucleotide complex, virus, polynucleotide-protein complex, or protein complex;

excising at least one fraction containing the at least one polynucleotide, polynucleotide complex, virus, polynucleotide-protein complex, or protein complex from the degradable polyacrylamide gel;

at least partially solubilizing the at least one excised fraction;

administering the at least one polynucleotide, polynucleotide complex virus, polynucleotide-protein complex, protein or protein complex to a cell, and measuring the functional activity of the at least one polynucleotide, polynucleotide complex, virus, polynucleotide-protein complex, protein or protein complex in the cell.

2. The method of claim 1, the at least one degradable cross-linker comprising the formula (II):

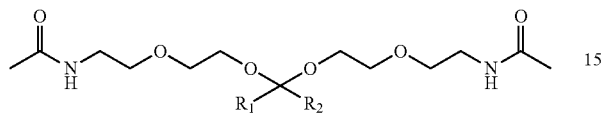

(II)

wherein $R_1$ and $R_2$ are the same or different and are hydrogen, an alkyl, or a substituted alkyl.

3. The method of claim 2, the alkyl being $C_1$-$C_5$ alkyl.

4. The method of claim 1, a polynucleotide or polynucleotide complex being administered to the cell.

5. The method of claim 4, the polynucleotide or polynucleotide complex being administered to the cells by transfecting the cells with the polynucleotide or polynucleotide complex.

6. The method of claim 1, a protein, protein complex or protein-polynucleotide complex being administered to the cells.

7. The method of claim 6, the protein, protein complex or protein-polypeptide complex being administered to the cells by nano-injection.

* * * * *